(12) United States Patent
Willner et al.

(10) Patent No.: US 6,630,309 B2
(45) Date of Patent: *Oct. 7, 2003

(54) DETERMINATION OF AN ANALYTE IN A LIQUID MEDIUM

(75) Inventors: Itamar Willner, Mevasseret Zion (IL); Shlomo Levi, Mevasseret Zion (IL); Yael Cohen, Mevasseret Zion (IL); Eugenii Katz, Jerusalem (IL); Arie Dagan, Jerusalem (IL)

(73) Assignees: Biosensor Applications Sweden AB, Sundbyberg (SE); Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 08/983,570

(22) PCT Filed: Jul. 16, 1996

(86) PCT No.: PCT/IL96/00049

§ 371 (c)(1),
(2), (4) Date: Jun. 4, 1998

(87) PCT Pub. No.: WO97/04314

PCT Pub. Date: Feb. 6, 1997

(65) Prior Publication Data

US 2002/0028440 A1 Mar. 7, 2002

(30) Foreign Application Priority Data

Jul. 21, 1995 (IL) ................................................. 114692

(51) Int. Cl.$^7$ ............................................ G01N 33/553
(52) U.S. Cl. ..................... 435/7.1; 422/57; 422/68.1; 422/82.01; 422/82.02; 422/82.03; 422/82.05; 422/82.11; 422/83; 422/98; 422/119; 422/186; 427/211; 427/212; 204/403; 204/406; 204/412; 204/416; 204/431; 204/222; 435/7.4; 435/7.5; 435/7.8; 435/287.9
(58) Field of Search ..................... 422/57, 68.1, 82.01, 422/82.02, 82.03, 82.05, 82.11, 83, 88, 98, 119, 186, 186.04, 186.06, 186.3; 427/211, 2.12; 204/403, 406, 412, 416, 431, 222, 900; 435/7.1, 7.4, 7.5, 7.8, 287.9, 288.7; 436/119, 73, 167, 151, 169, 501, 827, 805, 806, 807; 310/311, 312, 313 R, 313 A, 340, 314

(56) References Cited

U.S. PATENT DOCUMENTS 4,236,893 A   12/1980   Rice (List continued on next page.)

FOREIGN PATENT DOCUMENTS

EP   0668502   8/1995

(List continued on next page.)

OTHER PUBLICATIONS

Rickert et al., "A New Affinity Biosensor: Self–Assembled Thiols as Slective Monolayer Coating of Quartz Crystal Microbalances", *Biosensor & Bioelectronics*, 11:591–598, (1996).

(List continued on next page.)

*Primary Examiner*—Christopher L. Chin
*Assistant Examiner*—Pensee Do
(74) *Attorney, Agent, or Firm*—Browdy and Neimark, PLLC

(57) ABSTRACT

Binding between two members of a recognition pair, e.g. antigen-antibody is determined by utilizing a probe which includes a piezoelectric crystal with electrodes on two opposite faces of the crystal. The crystal carries one or more metal plates which may be the same or different than the electrodes, the metal plates having immobilized thereon a first member of a recognition pair. Binding of a second member of the recognition pair to the first member, or dissociation between the two members and release of the second member from the probe, causes a change of immobilized mass which results in a change to the probe's resonance frequency. The immobilized members may be immobilized on the surface of the metal plates by means of a linking group, having the following general formula (I): $Z-R^1-Q$, wherein Z represents a sulphur-containing moiety which is capable of chemical association with, attachment to or chemisorption onto the metal, $R^1$ represents a connecting group, Q is a functional group which is capable of forming a covalent bond with a moiety of said first member of the recognition pair.

14 Claims, 22 Drawing Sheets

U.S. PATENT DOCUMENTS

| | | | |
|---|---|---|---|
| 4,242,096 A | | 12/1980 | Oliveira et al. |
| 4,314,821 A | | 2/1982 | Rice |
| 4,735,906 A | | 4/1988 | Bastiaans |
| 4,999,284 A | * | 3/1991 | Ward et al. |
| 5,192,507 A | * | 3/1993 | Taylor et al. ............... 422/68.1 |
| 5,235,238 A | * | 8/1993 | Willner et al. ............... 204/193 |
| 5,242,828 A | * | 9/1993 | Bergstrom et al. .......... 435/291 |
| 5,514,501 A | * | 5/1996 | Tarlov ........................... 430/5 |
| 5,527,711 A | * | 6/1996 | Tom-Moy et al. .......... 436/518 |
| 5,552,274 A | * | 9/1996 | Oyama et al. .................. 435/6 |
| 5,583,432 A | * | 12/1996 | Barnes ........................ 324/204 |
| 5,595,908 A | * | 1/1997 | Fawcett et al. .............. 436/500 |
| 5,658,732 A | * | 8/1997 | Ebersole et al. ................ 435/6 |
| 5,695,925 A | * | 12/1997 | Ebersole et al. ................ 435/4 |
| 5,705,399 A | * | 1/1998 | Larue ........................... 436/501 |
| 5,852,229 A | * | 12/1998 | Josse et al. ................. 73/24.06 |
| 5,942,388 A | * | 8/1999 | Willner et al. ............... 204/193 |

FOREIGN PATENT DOCUMENTS

| | | |
|---|---|---|
| WO | 8909937 | 10/1989 |
| WO | 9105261 | 4/1991 |
| WO | 9402852 | 2/1994 |

OTHER PUBLICATIONS

Geddes, N. J., et al., "Surface Chemical Activation of Quartz Crystal Microbalance Gold Electrodes Analysis by Frequency Changes, Contact Angle Measurements and Grazing Angle FTIR," *Thin Solid Films*, 260:192–199 (1995).

Willner I. et al., "Photoregulated Binding of Spiropyran–Modified Concanaval in A to Monosaccharide–Functionalized Self–Assemble Monolayers on Gold Electrodes," *Journal of American Chemical Society*, 115:4937–4938 (1994).

Willner I. et al., "Application of Photoisomerizable Antigenic Monolayer Electrodes as Reversible Amperometic Immunosensors," *Journal of the American Chemical Society*, 116:9365–9366 (1994).

Engvall E. et al., "Enzyme Immunoassay ELISA and EMIT," *Method in Enzymology*, 70:419–439 (1980).

Muramatsu H. et. al., "Piezoelectric Immuno Sensor for the Detection of Candida albicans Microbes," *Analytica Chimica Acta*, 188:257–261 (1986).

Shon A. et al., "An Immunospecific Microbalance," *J. Biomed Mater. Res*, 6:565–571 (1972).

Suleiman A. et al., "Recent Development on Piezoelectric Immunosensor," *Analyst*, 119:2297–2282 (1994).

Ward M. et al., "In Situ Interfacial Mass Detection with Piezoelectric Transducers," *Science*, 249:1000–1007 1990.

Roederer J. et al., "Microgravimetric Immunoassay with Piezoelectric Crystal," *Anal. Chem.*, 55:2333–2336 (1983).

Muramatsu H. et al., "Piezoelectric Crystal Bisensor Modified with Protein A for Determination of Immunoglobulins," *Anal. Chem.*, 59:2760–2763 (1987).

Muramatsu H. et al., "Piezoelectric Crystal Biosensor System for Detection of *Escherichia Coli*," *Analytical Letters*, 22(9):2155–2166 (1989).

Konig B. et al., "Detection of Viruses and Bacteria with Piezoelectric Immunosensors," *Analytical Letters*, 26(8):1567–1585 (1993).

Mueller–Shulte D. et al., "Preparation of Piezoelectric Biosensor for Determination of Antigens and Affinity Ligands," *Chemical Abstracts*, 112:51807 (1990).

* cited by examiner

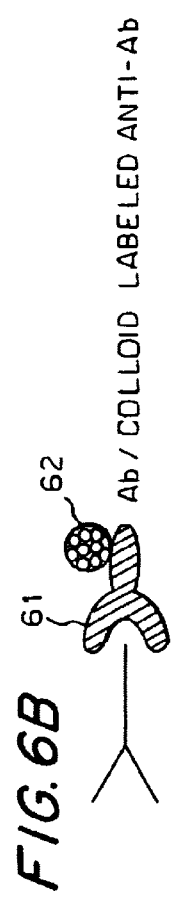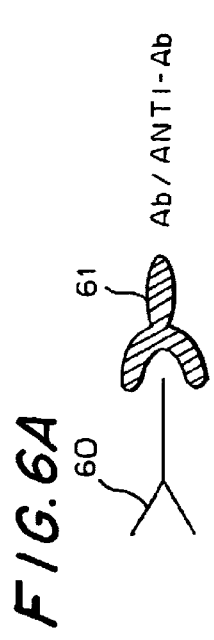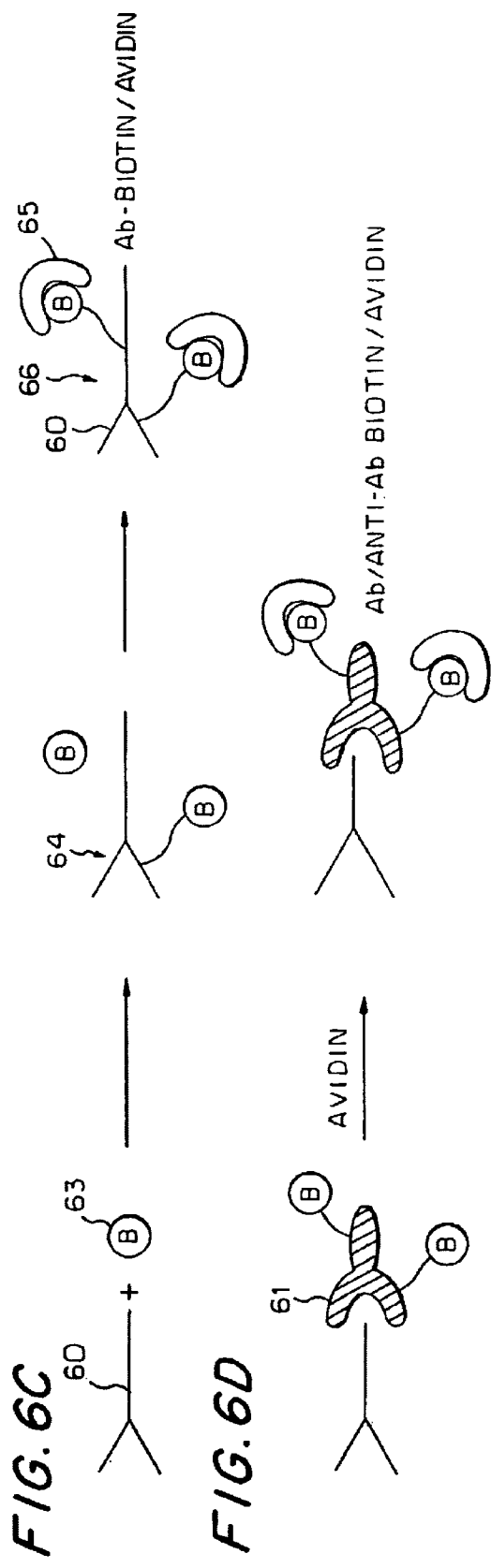
FIG.6A
FIG.6B
FIG.6C
FIG.6D

FIG. 9A
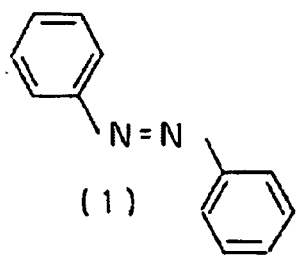
(1)
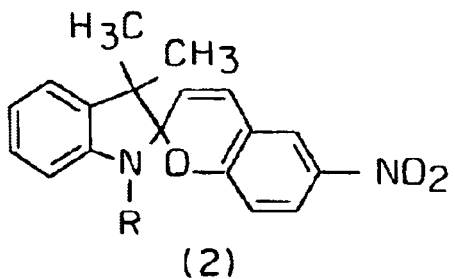
(2)
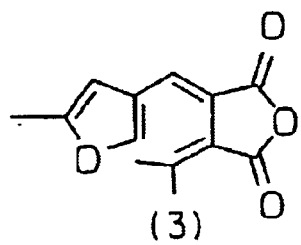
(3)
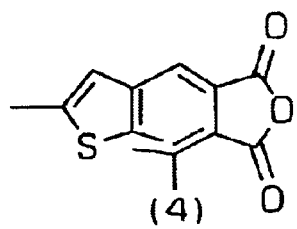
(4)
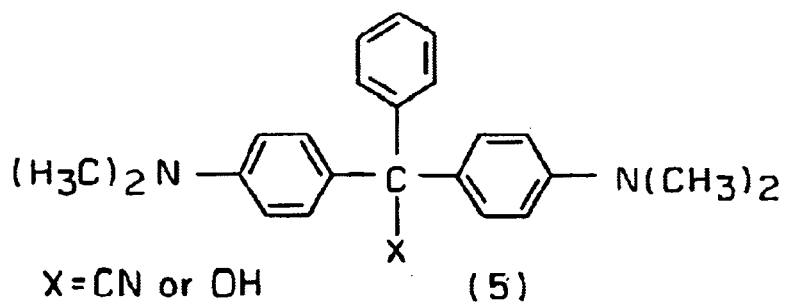
X = CN or OH    (5)

FIG. 9B
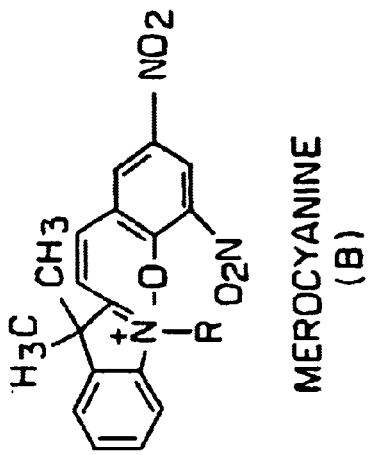
MEROCYANINE (B)
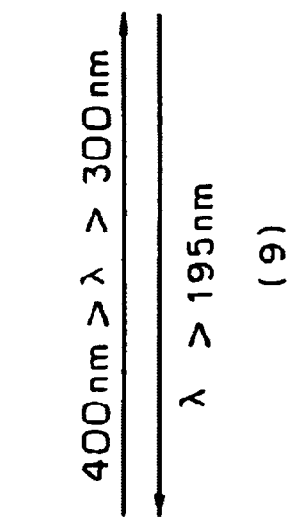
$400nm > \lambda > 300nm$
$\lambda > 195nm$
(9)
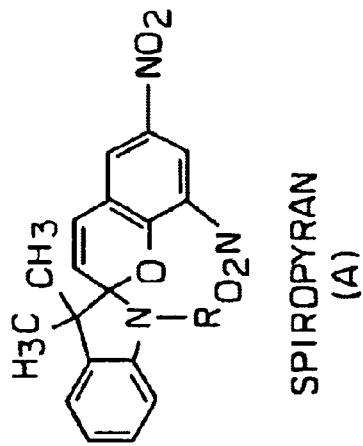
SPIROPYRAN (A)
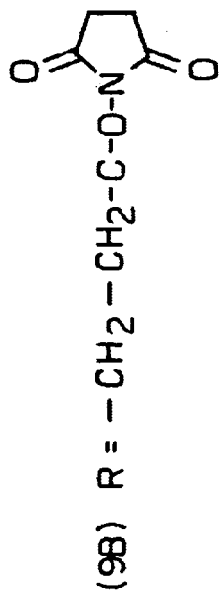
(9A) R = —CH$_3$
(9B) R = —CH$_2$—CH$_2$—CH$_2$—C—O—N

FIG. 9D
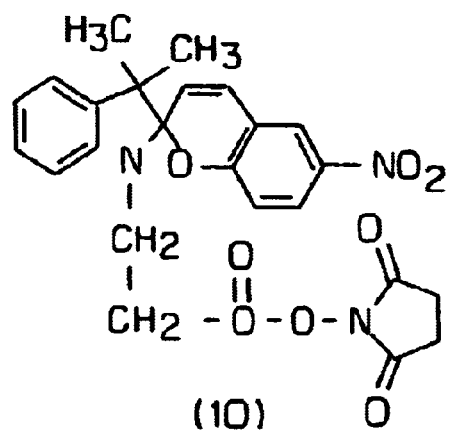
(10)
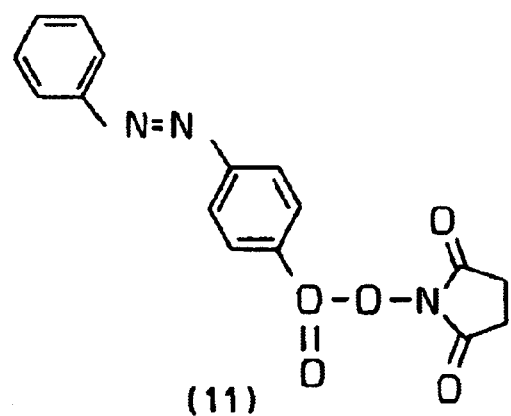
(11)
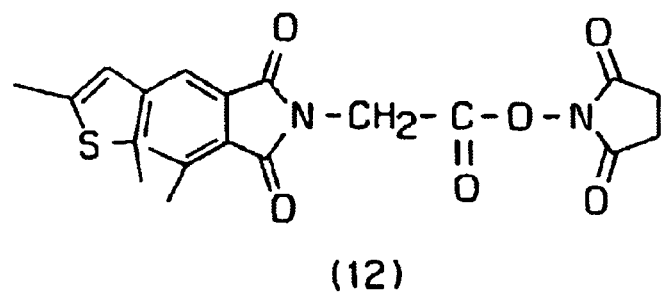
(12)

DETERMINATION OF AN ANALYTE IN A LIQUID MEDIUM

FIELD OF THE INVENTION

The invention is generally in the field of biosensors, and concerns a sensor useful for the determination of the presence, and optionally also concentration, of an analyte in a liquid, particularly aqueous, medium. The present invention relates to such electrodes, as well as their use and systems comprising them.

PRIOR ART

In the following description, reference will be made to several prior art documents shown in the list of references below. The reference will be made by indicating their number from this list.

References
1. E. Engvall, in: *Methods in Enzymology*, Vol. 70, 1980, pp. 419–439.
2. A. Shons, F. Dorman, J. Najarian, *J. Biomed. Mater. Res.* 6, 565 (1972).
3. A. A. Suleiman and G. G. Guilbault, *Analyst*, 119, 2279 (1994).
4. M. D. Ward and D. A. Buttry, *Science,* 249, 1000 (1990).
5. J. R. Oliveria and S. F. Silver, U.S. Pat. No. 4,242,096 (1980).
6. T. K. Rice, U.S. Pat. No. 4,236,893 (1980).
7. T. K. Rice, U.S. Pat. No. 4,314,821 (1982).
8. J. E. Roederer, G. J. Bastiaans, *Anal. Chem.,* 55, 2333 (1983).
9. J. E. Roederer and G. J. Bastiaans, U.S. Pat. No. 4,735,906 (1988).
10. H. Muramatsu, J. M. Dicks, E. Tamiya and I. Karube, *Anal. Chem.,* 59, 2760 (1987).
11. D. Mueller-Schulte and H. Laurs, CA. 1990, 112(7), 51807 g.
12. H. Muramatsu, K. Kajiwara, E. Tamiya and I. Karube, *Anal. Chim. Acta,* 188, 257 (1986).
13. H. Muramatsu, Y., Watanabe, M. Hikuma, T. Ataka, I. Kubo, E. Tamiya and I. Karube, *Anal. Lett.,* 22, 2155 (1989).
14. B. Konig and M. Grätzel, *Anal. Lett.,* 26, 1567 (193).
15. M D. Ward and R. C. Ebersole, PCT Application, Application No. WO 89/09937.
16. R. C. Ebersole, R. P. Foss and M. D. Ward, PCT Application, Application No. WO/94/02852.
17. R. C. Ebersole and J. R. Moran, PCT Application, Application No. WO/91/05251.
18. N. J. Geddes, E. M. Paschinger, D. N. Furlong, F. Caruso, C. L. Foffmann and J. F. Rabolt, *Thin Solid Films*, 260:192–199 (1995).
19. I. Willner, S. Rubin and Y. Cohen, *J. Amer. Chem. Soc.,* 115:4937–4938, (1993).
20. I. Willner, R. Blonder and A. Dagan, *J. Amer. Chem. Soc.,* 116:9365–9366, (1994).

Mention of the above references in this writing does not mean to imply that these references are in any way relevant to the issue of patentability of the invention as defined in the appended claims.

BACKGROUND OF THE INVENTION

The specificity of antigen-antibody binding interactions and the technological progress in eliciting monoclonal antibodies for low molecular weight materials provide the grounds to design sensitive immunosensor devices for clinical diagnostics, food control and environmentally polluting substances. The most extensively developed immunosensor analyses include radioisotopic antigen/Ab labels and enzyme-linked immunosorbant assays (ELISA)[1].

The discovery of a linear relationship between the change in the oscillating frequency of a piezoelectric crystal and the mass variation on the crystal as a result of binding or adsorption phenomena opened the possibilities to monitor gravimetrically antigen-antibody binding phenomena. The mathematical relation between the frequency changes of a piezoelectric crystal, $\Delta f$, and mass changes, $\Delta m$, on the crystal is given by the following Sauerbrey equation:

$$\Delta f = -2.3 \times 10^6 f_o^2 \cdot \Delta m / A$$

where $f_o$ is the fundamental resonance frequency of the crystal prior to the mass variation and A is the surface area of deposited mass. For example, for a crystal exhibiting a fundamental frequency of 9 MHz and surface area of 1 cm$^2$, a mass-change on the crystal that corresponds to $1 \times 10^{-9}$ g will stimulate a frequency change, $\Delta f$, of 6 Hz.

The first analytical use of piezoelectric crystals in relation to antigen-antibody (Ag—Ab) interactions was reported in 1972[2], where a nyebar precoated crystal was further coated via hydrophobic interactions, with bovine serum albumin (BSA) and the association of the BSA—Ab to the crystal was monitored by the frequency changes. Since then, the piezoelectric detection of antigens and antibodies by piezoelectric means or the quartz crystal microbalance (QCM) has been adopted in a series of analytical studies. The progress in this area has been reviewed by Suleiman et al., 1994[3] and Ward et al., 1990[4]. Immobilization of an antibody on a QCM device has been described by Geddes et al.[18].

Several patents describe the application of QCM for the analysis of antigens and antibodies. Physical adsorption of antigens to a crystal was used as a means for the detection of antigens by interacting the crystal with a mixture of the analyte antigen and a predetermined amount of Ab[5]. The decrease in the antigen concentration was inversely related to the antigen concentration in the sample. In two patents by Rice[6,7], methods for the determination of Abs by QCM were disclosed. The antigen was immobilized on a polymer precoated crystal and the frequency changes as a result of Ab association related to the analyte Ab concentration in the sample. By this method, human IgG against honey bee venom, phospholipase A, and keyhole limpet hemocyanine were analyzed[6]. However, non-specific binding to the crystal interfered with the analyses. In a follow-up patent[7], the detection of low molecular weight components by a pre-coated crystal with the anti-Ab and competitive binding assay of the Ab-low molecular weight analyte was described. All of these analyses were performed by treatment of the crystals in solution and subsequent frequency measurements in air. This two-step solution/gas procedure allows improvement of the sensitivity of the resonating QCM, but introduces technical complications and the interference of hydration/dehydration phenomena that are reflected in the frequency parameters. Ward et al. [15] and Ebersole et al. [17] disclose a QCM assay where the sensitivity is increased by the use of an enzyme comprising conjugates which binds to the analyte after the latter has been bound to a capturing agent, which enzyme catalyzes a reaction where a substrate is converted to the product and the product which is absorbed on the QCM increases the mass of the QCM which gives rise to a change in its resonance frequency. Ebersole et al.[16] discloses a method that makes use of a polymer which changes its mass in the presence of an analyte, e.g. H$^+$ ions (serving as a pH) sensor.

Piezoelectric immunoassaying in the liquid phase has important technical advantages as it allows stationary and flow analysis of aqueous samples. The method suffers, however, from a basic physical limitation due to substantially lower frequency changes of the crystal as a result of the solution viscosity. QCM immunoassays in solution were reported by Roederer[8] and addressed in a follow-up patent [9]. The quartz crystal was modified with glycidoxypropyl-trimethoxy silane (GOPS), and the surface-modified crystal was then further modified by anti-human IgG antibody and then applied for the piezoelectric detection of human IgG. The detection limit of the device was determined to be 13 $\mu g \cdot ml^{-1}$. A closely related approach was adopted by Muramatsu et al.[10] where the quartz crystals were surface-modified by γ-aminopropyl triethoxy silane and further derivatized by protein A. The surface-modified crystals were then applied for the determination of human IgG in the concentration range $10^{-6}$–$10^{-2}$ $mg \cdot ml^{-1}$. A related patent disclosed the piezoelectric analysis of thyroxine using a polyamide 6 polymer coating and anti-thyroxine Ab as sensing interface[11].

Piezoelectric analysis of high molecular weight antigens such as microbial cells was addressed using antibody-coated quartz crystals. *C. albicans* cells in the concentration range $1 \times 10^6$–$5 \times 10^8$ $cells \cdot ml^{-1}$ were analyzed by an anti-*Candida albicans* Ab surface (12), *E. coli* with an anti-*E. coli* interface[13] and protein A-coated crystals acted as piezoelectric sensing interface for various bacteria including Salmonella, Shigella, Yersinia and *E. Coli*[14].

Use of photoisomerizable substance for the photoregulated binding of molecules to a substrate has been described by Willner et al.[19] The aplication of this feature in reversible amperometric immunosensors has been described by Willner et al.[20]

Methods utilizing piezoelectric devices allow immunochemical sensing of interactions between two members of a recognition pair such as Ab—Ag, sugar-lectin, biotin-avidin, etc., without the need for labeling, and provide competitive analytical tools to conventional radio-labeled and enzyme-labeled analyses.

GENERAL DESCRIPTION OF THE INVENTION

It is an object of the present invention to provide a method for determining the presence and optionally the concentration of analyte in a liquid medium, analyte being a member of a recognition pair.

It is further an object, in accordance with an embodiment of the present invention, to provide a system for carrying out the above method.

It is furthermore an object of the present invention to provide electrodes for use in the above system and method.

It is still further an object of the present invention to provide a process for the preparation of such electrodes.

The present invention makes use of a piezoelectric crystal and determining a change in mass bound to the crystal by measuring a change of its resonance frequency. In the following, the term "Δf response" will be used to denote a change of frequency of the electrode as the result of binding of a mass thereto or release of a mass therefrom.

In accordance with the present invention, a novel system and an electrode for use in the system are provided. The system in accordance with the present invention is capable, by means of a Δf response, to determine the presence and optionally the concentration of an analyte in a liquid medium. The analyte is a member of a pair of molecules or complexes of molecules, which can specifically bind to one another in a non-covalent manner. Such a pair of molecules will be referred to herein as "recognition pair". The recognition pair may consist for example of antigen-antibody, ligand-receptor, sugar-lectin, biotin-avidin, enzyme-substrate, oligonucleotide-oligonucleotide with a complementary sequence, oligonucleotide-protein, olignucleotide-cell, etc.

In the following description the terms "determination" or "determine" will be used to denote both qualitative and quantitative determination of binding. Where, for example, the method and system defined below are used for determining an analyte in a liquid medium, this is meant to denote determining the presence of an analyte in the medium and optionally its concentration. In other words, a Δf response will be used as a qualitative measure for the presence of the analyte in a medium; the extent of the Δf response will be used as a measure of the amount of analyte in a tested medium.

The term "analyte" already used above and which will be used further below, is meant to denote an unknown agent determined in a liquid medium.

The present invention has several aspects. One such aspect concerns a system for determining binding between two members of a recognition pair ("system aspect"); another such aspect relates to a method for determining such binding, which may be used for testing an analyte in a medium ("method aspect"); a further aspect is concerned with probes for use in the above system and method ("probe aspect"); and a further aspect is concerned with a process for the preparation of such a probe ("process aspect").

In accordance with the system aspect of the present invention, there is provided a system for determining binding between two members of a recognition pair, comprising:

(a) a probe comprising a piezoelectric crystal, electrodes on two opposite faces of the crystal, and one or more metal plates carried on the surface of said crystal, said metal plates being the same or different than said electrodes, the metal plates having immobilized thereon a first member of a recognition pair, binding of a second member of the recognition pair to the first member, or dissociation between the two members and release of the second member from the probe, causing a change of mass resulting in a change to the probe's resonance frequency;

(b) a vessel for holding a liquid, the probe being immersed in the liquid to allow either
   binding between the first, immobilized member and the second member dissolved in the liquid, or
   release of the second member, a priori bound to said first member, into said liquid; and (c) electric or electronic circuitry for generating an alternating electric field between said electrodes, and measuring of the resonance frequency of said crystal.

In accordance with an embodiment of the method aspect of the invention, there is provided a method for determining binding between a first member of a recognition pair and a second member of a recognition pair, the second member being a priori contained in a liquid medium, comprising:

(a) providing a probe comprising a piezoelectric crystal, electrodes on two opposite faces of the crystal, and comprising one or more metal plates carried on the surface of said crystal, said plates being the same or different than said electrodes, the first member of the recognition pair being immobilized on the said plates;

(b) measuring an initial resonance frequency of the probe;

(c) contacting said probe with a liquid medium containing said second member for a time sufficient to allow binding between the two members; and (d) measuring a second resonance frequency, a lower second resonance frequency as compared to the initial resonance frequency indicating the presence of said second member in the liquid medium.

In accordance with another embodiment of the method aspect, there is provided a method for determining an analyte in a liquid medium, comprising:

(a) providing a probe comprising a piezoelectric crystal, electrodes on two opposite faces of the probe, and comprising one or more metal plates carried on the surface of said crystal, said metal plates being the same or different than said electrodes, the metal plates having immobilized thereon a first member of a recognition pair, the second member of said pair being non-covalently bound to said first member, said second member being capable of binding to said analyte, the binding between said second member and said analyte being competitive to the binding of said second member to said immobilized member;

(b) measuring an initial resonance frequency of the probe;

(c) contacting said probe with said liquid medium under conditions and for a time such that in the presence of said analyte, at least some of said second member will be released from the electrode and bind to said analyte; and (d) measuring a second resonance frequency, a higher second resonance frequency as compared to the initial resonance frequency indicating the presence of said analyte in said medium.

In accordance with a further embodiment of the method aspect, there is provided a method for determining an analyte in a liquid medium, comprising:

(a) providing a probe comprising a piezoelectric crystal, electrodes on two opposite faces of the crystal, and comprising one or more metal plates carried on the surface of said crystal, said metal plates being the same or different than said electrodes, said metal plates having immobilized thereon a first member of a recognition pair; the pair comprising a second member being capable of binding to said analyte, the binding between said second member and said analyte being competitive to the binding of said second member to said immobilized member;

(b) measuring an initial resonance frequency of the probe;

(c) mixing said liquid medium with a solution containing said second member, the presence of said analyte in the medium causing binding thereto of said second member;

(d) contacting the mixture obtained in step (c) with said probe for a time sufficient to allow binding of said second member to the immobilized first member; and (e) measuring a second resonance frequency of the probe, a second resonance frequency lower than the initial frequency indicating pressence of said analyte in the liquid medium (a relatively large decrease in resonance frequency meaning no or a small amount of analyte in the liquid medium; no or a small decrease in resonance frequency meaning a relatively large amount of the analyte in the liquid medium).

In accordance with the probe aspect of the invention there is provided a probe for use in the above method and system. The probe comprises a piezoelectric crystal having electrodes on two opposite faces of the crystal, and one or more metal plates carried on the surface of said crystal, said metal plates being the same or different than said electrodes, the metal plates having immobilized thereon a first member of a recognition pair.

In order to cause a piezoelectric crystal to vibrate and eventually reach resonance frequency, the piezoelectric crystal has to be subjected to an alternating electrical field. The piezoelectric crystal used in accordance with the invention is typically a planar crystal having the form of a plate or a disc, and the electrodes which provide the alternating electrical field are typically planar metal electrodes attached to opposite faces of the crystal. The plates with the immobilized member of a recognition pair are preferably the same as the planar electrodes, in other words the electrodes serve both for the provision of an alternate electrical field and for immobilization of said first member.

An embodiment in accordance with the present invention where the analyte is measured directly by binding to the first member immobilized on the probe, will be referred to herein as "direct embodiment". A direct embodiment is an embodiment where the analyte to be determined is the second member of the recognition pair. An embodiment in accordance with the invention, such as the second and third embodiments defined above, where the presence of analyte is measured indirectly, i.e. what is measured in essence is the depletion of the second member will be referred to herein as the "indirect embodiment".

The method in accordance with the direct embodiment can be practiced in particular where the second member is a relatively large molecule or a complex of molecules, the binding of which to the immobilized member causing a considerable mass change. Where the analyte is a small molecule, it is usually preferred to practice the invention by an indirect embodiment, since binding of such an analyte to the probe will bring about only a very small change of mass. The second member in such a case will typically be a large molecule, e.g. an antibody with a binding affinity to said analyte.

An example of the direct embodiment of the invention is the determination of an antibody in a biological sample in which case the electrode has immobilized thereon an antigen to which said antibody specifically binds; or the determination of a protein antigen by the use of an electrode having immobilized thereon an anti-antigen antibody.

In accordance with the indirect embodiment, the immobilized member may be an immobilized analyte molecule or a molecule with a similar binding specificity to said second member as said analyte. Preferably, the immobilized analyte molecule has a lower binding affinity to said second member than the analyte, to allow effective depletion of said second member in the presence of the analyte.

An example of the indirect embodiment is the use of an immobilized antigen in order to determine an identical or related antigen in a biological sample to be tested. In accordance with this specific example, the biological sample, e.g. a plasma sample is first reacted with a reagent solution comprising an antibody which specifically binds to the antigen to be determined. After binding, the concentration of free (unbound) antibody becomes lower. Following an incubation period, a probe having antigen molecules immobilized thereon (the immobilized antigen, in this case being said immobilized member) is challenged with the reacted solution, and the determination of the free antibody then serves as an indication of said antigen in the tested biological sample. As will no doubt be appreciated by the artisan, the concentration of said free antibody will be in opposite correlation to the concentration of the antigen in the tested sample.

Furthermore, as will also be appreciated, an antibody in a tested biological sample rather than an antigen may be determined in an analogous manner, mutatis mutandis.

The analyte may at times also be a molecule suspended or dissolved in a gas, e.g. various airborne chemicals. In such a case, a gas suspected of containing an analyte is first passed (e.g. "bubbled") through a suitable liquid which can dissolve the analyte, and this liquid is then tested for the presence of the analyte therein. Obviously, as gaseous chemicals are typically small molecules, determining of such analyte is preferably carried out by the indirect embodiment.

At times, in order to increase sensitivity, rather than determining the Δf response within the liquid, the probe is first dried and then the measurement of Δf is performed with the probe embedded in a gas or in a vacuum.

The recognition pair, of which a first member is immobilized on the probe's metal plate, may, for example, be an antigen-antibody, sugar-lectin, ligand-receptor, biotin-avidin, enzyme-substrate, oligonucleotide-complementary oligonucleotide, oligonucleotide-protein, and oligonucleotide-cell, and generally any pair of molecules with specific binding affinity to one another.

As a result of binding of the second member to the immobilized first member or the dissociation of the two members and the release of the second member from the probe, there is a change in mass which in turn results in a change in the resonance frequency (i.e. Δf response). The degree of Δf response correlates with the extent of binding or release of said second member and depends on the concentration of said analyte in the tested liquid surrounding the electrode. Thus, the extent of change in the resonance frequencies may be used, in accordance with a preferred embodiment of the invention, as an indication of the concentration of said analyte in the medium.

The metal plates carrying said immobilized member may be selected from a variety of metals, particularly such having the capability to associate chemically with, attach or chemisorb a sulphur-containing moiety. The metal plates are preferably made of or coated by metals such as gold, platinum, silver or copper.

The immobilized member is preferably immobilized on the surface of the metal plate by means of a linking group, which typically may have the following general formula (I):

$$Z-R^1-Q \quad \quad (I)$$

wherein:

Z represents a sulphur-containing moiety which is capable of chemical association with, attachment to or chemisorption onto said metal;

$R^1$ represents a connecting group;

Q is a functional group which is capable of forming a covalent bond with a moiety of said first member of the recognition pair.

Z may for example be a sulphur atom, obtained from a thiol group, a disulphide group, a sulphonate group or sulphate groups.

$R^1$ may be a covalent bond or may be a peptide or polypeptide or may be selected from a very wide variety of suitable groups such as alkylene, alkenylene, alkynylene phenyl containing chains, and many others.

Particular examples of $R^1$ are a chemical bond or a group having the following formulae (IIa), (IIb), (IIc) or (IId):

II (a)

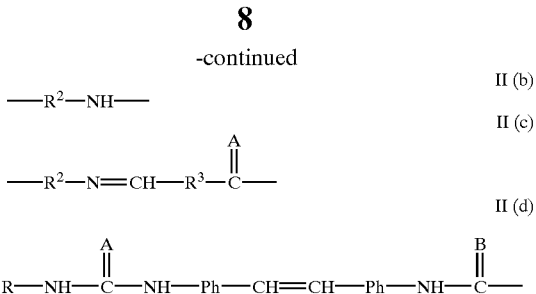

wherein $R^2$ or $R^3$ may be the same or different and represent straight or branch alkylene, alkenylene, alkynylene having 1–16 carbon atoms or represent a covalent bond, A and B may be the same or different and represent O or S, Ph is a phenyl group which is optionally substituted, e.g. by one or more members selected from the group consisting of $SO_3^-$ or alkyl groups.

Q may for example be a functional group capable of binding to a carboxyl residue of a member of a recognition pair such as an amine group, a carboxyl group capable of binding to amine residues of the member of a recognition pair; an isocyanate or isothiocyanate croup or an acyl group capable of binding to an amine residue of the member of a recognition pair, or a halide group capable of binding to hydroxy residues of the protein or a polypeptide. Particular examples are the groups $-NH_2-COOH$; $-N=C=S$; $N=C=O$; or an acyl group having the formula $-R^a-CO-G$ wherein G is a halogen such as Cl or OH, $OR^b$, a

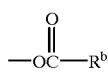

group or a

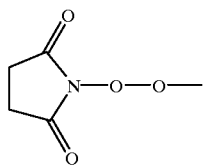

group; $R^a$ and $R^b$ being, independently a $C_1-C_{12}$ alkenyl, alkenyl or a phenyl containing chain which is optionally substituted, e.g. by halogen.

Particular examples of such a linking group are cysteamine (III), cystamine (IV) and cysteic acid N-hydroxysuccinimide ester (V) having the formulae:

(III)

(IV)

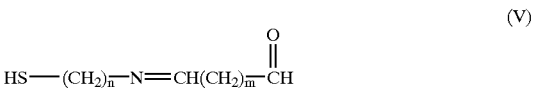

(V)

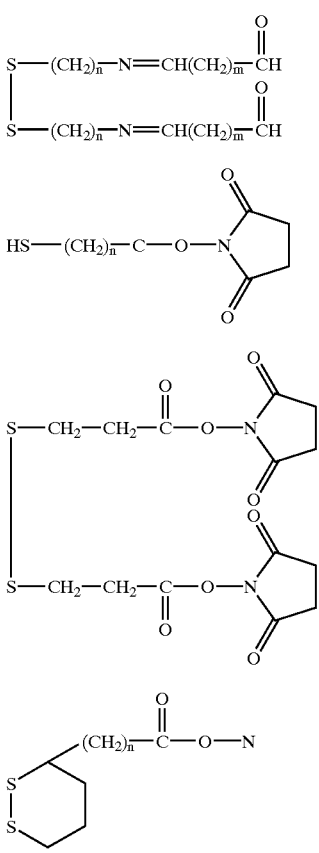

wherein n and m are integers between 1–24, preferably 1–12 and most preferably 1–6.

The sensitivity of the method of the invention may be increased by the use of a molecule, moiety or a complex, which is complexed or bound to said second member. Such a sensitivity increasing moiety, molecule or complex will be referred to herein as "amplifier group". The amplifier group may be a molecule or a complex having a binding affinity to said second member. Such an amplifier group may be made to bind to said second member after same has bound to the immobilized member or prior to such binding. The binding or complexing of the amplifier group to said second member will increase the mass change as a result of binding of said second member, or dissociation and release of said second member, as the case may be, and accordingly there will be a more noticeable Δf response, and hence an increase in sensitivity.

By increasing the sensitivity of the system in the manner described above, a Δf response can be measured even after binding or release of only a few second member molecules to the probe.

Binding of two members of a binding couple to one another is typically a high affinity binding, namely the two members do not dissociate easily from one another and even after proper rinsing, the second member may still remain substantially bound to the first immobilized member. In order to re-use the probe for a further measurement, there is a need to dissociate the second member from the immobilized member and remove it from the system. In accordance with an embodiment of the invention, the dissociation is achieved by means of a group, attached to the immobilized member which has two isomerization states and is capable of switching reversibly between its two states by exposure to two different types of energy ("isomerizable group"). Such an isomerizable group will typically have a first and second isomerization state and by reversibly switching from one state to the other, each such switching achieved with a different energy type, will cause a conformational change in the immobilized member which will bring about a change in the binding of affinity of the immobilized member to said analyte. Such a conformational change may, for example, be the occlusion of the binding site or a conformational change within the binding site which will cause a reduction in the binding affinity of the immobilized member to the second member. Such a reduction in affinity or vice versa may be defined as change or switch from a state of high affinity to a state of low, affinity or vice versa. In the first state, the immobilized member will have a high affinity to binding to the second member and after performing a measurement, the probe will be treated so that said isomerizable group will switch to the second state and consequently said second member will dissociate from the immobilized member. After removal of said analyte from the system, typically by rinsing and washing away of the rinsing solution, the probe will be further treated so that said isomerizable group switches back to said first state, whereby the probe will be ready for re-use.

The switching between the two states may be achieved by exposure to light of an appropriate wavelength within the infra red, visible or ultra violet range. The reactive isomerizable group will switch from said first state to said second state by exposure to light energy at a first wavelength and from a second state to said first state by exposure to a second, different than the first, wavelength. It is also possible that one of the switches will be achieved by mild thermal treatment.

Thus, in accordance with an embodiment of the invention the immobilized member of the recognition pair has or is linked to an isomerizable group reactive to exposure to light energy; said group having a first and a second state and is capable of being converted from the first state to the second state by exposure to irradiation of light of a first wavelength and from the second to the first state by exposure to irradiation of light of a second wavelength; the exposure inducing a change in affinity of the immobilized member for binding to said second member, whereby in the first state said immobilized member has a high affinity of binding to said second member such that said second member remains essentially bound to the immobilized member and in said second state said immobilized member has a low affinity of binding to said second member, such that the bound said second member is readily dissociated.

According to another embodiment of the invention said switching from the first state to the second state is by exposure to light energy but the switching from said second state to said first state is by mild thermal treatment.

In accordance with the process aspect of the invention, there is provided a process for preparing a probe for use in the above method and system, comprising:

(a) immobilizing said linking group onto the plate by chemical association attachment or chemisorption of the sulphur-containing moiety (Z); and (b) binding the member of the recognition pair to be immobilized to said functional group (Q).

Steps (a) and (b) may also be reversed so that immobilization takes place before binding.

The process aspect of the invention further provides a process for preparing a probe carrying immobilized members which are attached to an isomerizable group, the process comprising:

(a) immobilizing said linking group onto the said plate by chemical association attachment or chemisorption of the sulphur-containing moiety;

(b) chemically modifying a member of said recognition pair with a photoisomerizable group whereby the modified member changes its binding affinity to the other member of the recognition pair by exposure to energy; and (c) binding the modified member of the recognition pair to said functional group of the linking group immobilized on the electrode.

Steps (b) and (c) can be reversed such that the isomerizable group is bound to the member of the recognition pair after it has been immobilized in the electrode and so can steps (a) and (b).

The invention will now, be illustrated in the following description of some specific embodiments, with occasional reference to the annexed drawings, without prejudice to the generality of the foregoing.

DESCRIPTION OF THE DRAWINGS

In the drawings:

FIG. 6 shows a possible configuration of Ab-conjugate complexes;

DETAILED DESCRIPTION OF THE INVENTION

The invention will now be illustrated by several specific embodiments, it being understood that these are given as examples only and that the invention is not limited thereto.

Figure 1:
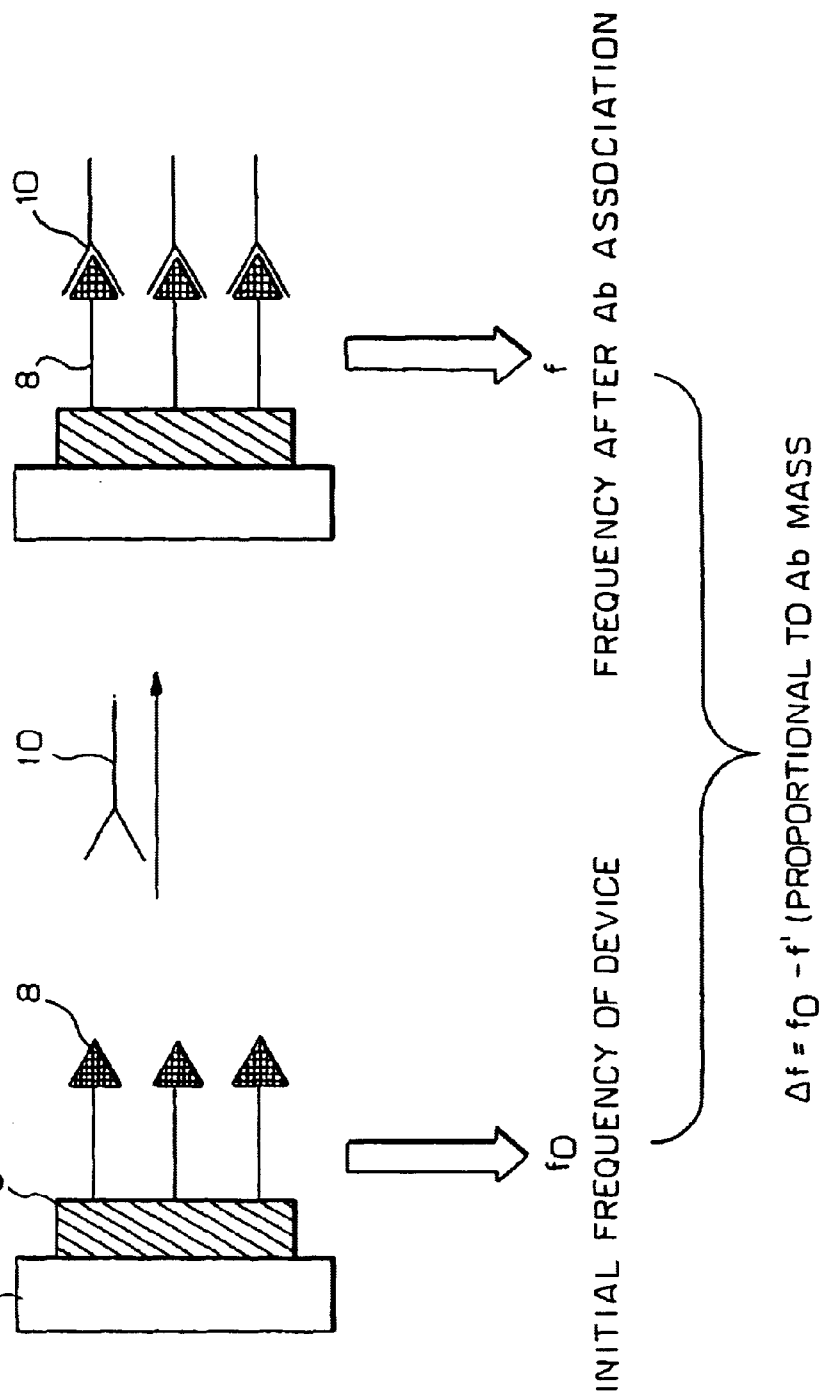
FIG. 1 shows a scheme of QCM for antibody analysis.

Reference is first being made to FIG. 1 showing a schematic representation of a manner of carrying out the invention according to the direct embodiment. A probe, generally designated 2, comprises a piezoelectric crystal 4 and two gold electrodes 6 (for simplicity, only one electrode is schematically shown while another electrode is positioned on the opposite face of the crystal). Immobilized on the electrode are a plurality of antigens 8 which are members of a recognition pair, the pair consisting of these antigens and antibodies 10 which latter is the analyte to be determined. Electrodes 6, as well as the corresponding electrodes in the other embodiments shown and described below, are connected to an electric or electronic circuitry (not show n) for generating alternating current between the pair of electrodes 6 and for measuring the resonance frequency of the electrodes.

Prior to determination of the analyte, an initial resonance frequency of the sensing member, is determined ($f_0$). Then, the probe 2 is challenged with a liquid containing the antibodies 10 which, if present in the liquid bind to the immobilized antigen 8.

Consequently, there is a change in mass and an accompanying change, $\Delta f$, in resonance frequency. $\Delta f$ is proportional to the mass of the bound antibodies, which in turn is proportional to the initial concentration of the antibodies in the tested liquid medium.

In a similar manner, mutatis mutandis, it is possible also to determine the concentration of an antigen in a liquid medium, by having the antibodies immobilized on the surface of the electrodes, particularly where the antigens are relatively large molecules, e.g. proteins.

Figure 2:
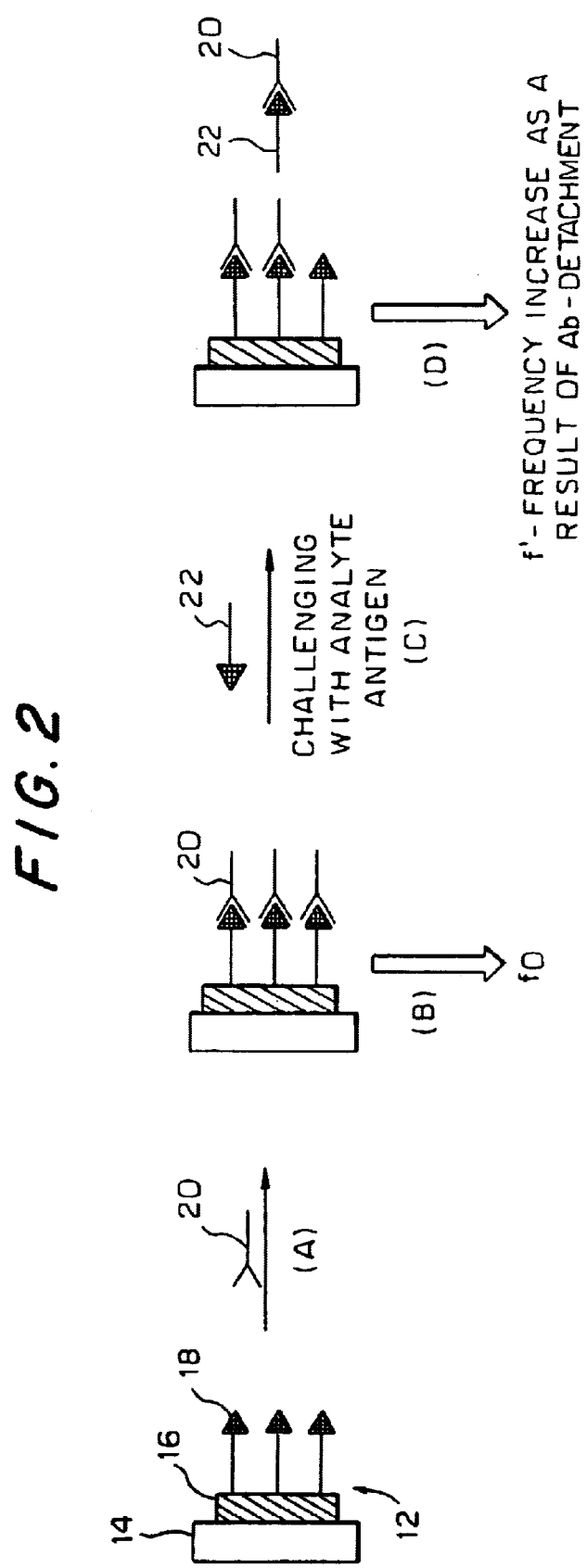
FIG. 2 shows a scheme for QCM analysis of an antigen by a QCM probe modified with an antigen monolayer and saturated with the Ab.

Reference is now being made to FIG. 2, shouting a manner of carrying out the invention in accordance with the indirect embodiment. A probe 12 of this embodiment comprises a piezoelectric crystal 14 carrying gold electrodes 16, having immobilized thereon antigens 18 (similarly as above the electrodes are connected to an electric or electronic circuitry for passing current and measurement of resonance frequency). In a first step (A), the sensing member is contacted with a medium comprising a large amount of antibodies 20, which bind to the immobilized antigens, the amount of antibodies being sufficient to permit binding to saturation. At this stage, resonance frequency, $f_0$, of the sensing member is determined (B). The sensing member is then challenged (C) with a liquid medium containing analyte 22 to be determined, which is capable of specific binding to antibody 20, with a similar or at times larger binding affinity than that of the antibody 20 to immobilized antigen 18. As a result of binding competition with the immobilized member, some of the bound antibodies 20 are released, and consequently there is a reduction in the immobilized mass and a resulting increase in the resonance frequency (D). This increase will be proportional to the amount of released mass, which is in turn proportional to the amount of agent in the tested liquid medium.

Figure 3:
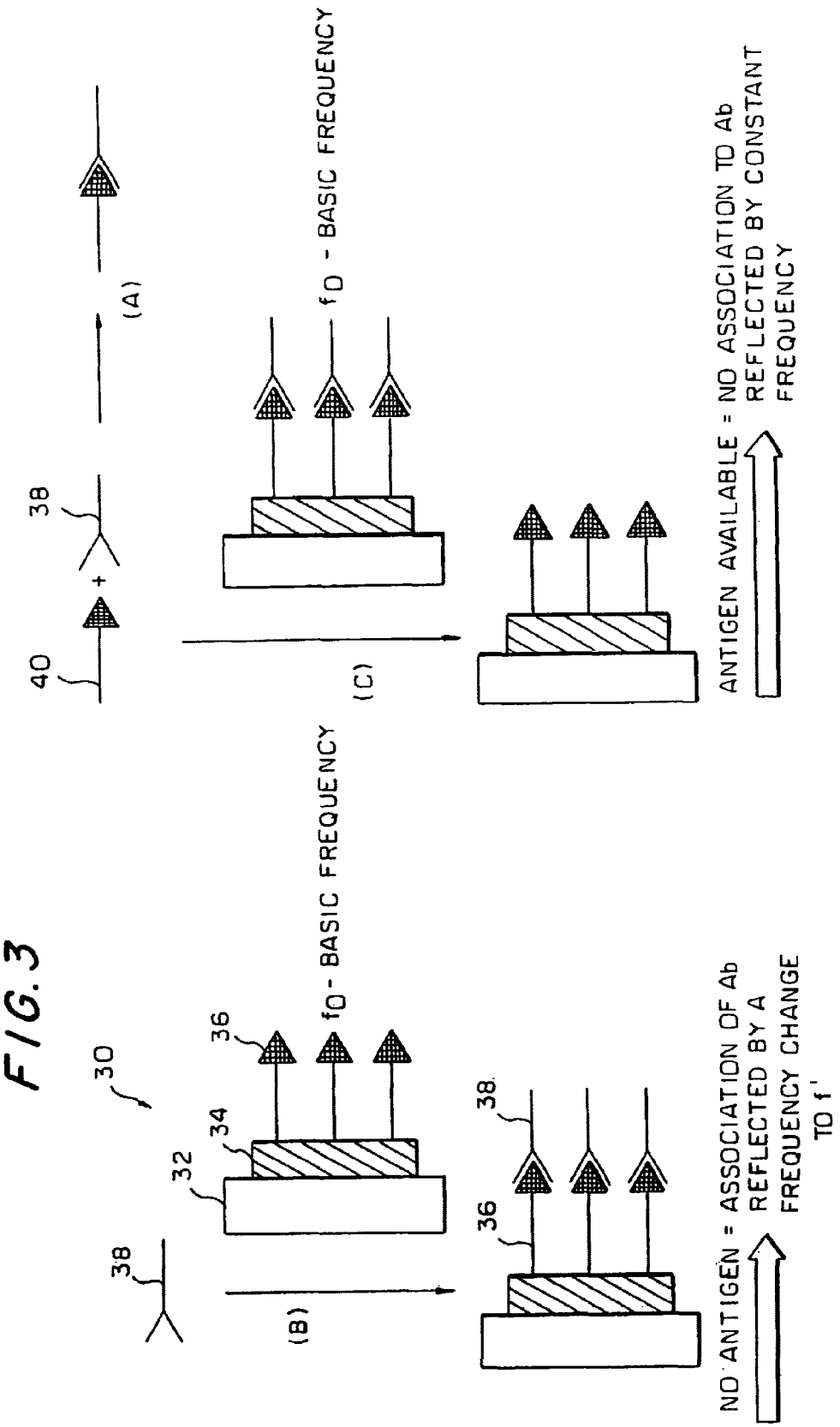
FIG. 3 shows a scheme for QCM analysis of an antigen by treatment of an antigen monolayer QCM probe with a mixture consisting of the analyte antigen and a constant, predetermined Ab concentration.

Reference is now being made to FIG. 3, showing an alternative embodiment of carrying out the invention according to the indirect embodiment. The probe 30 according to this embodiment comprises, similarly as before, piezoelectric crystal 32 carrying gold electrode 34 with immobilized antigens 36. Antigen 36 is a member of a recognition pair, the other member being antibody 38.

The system shown in FIG. 3 serves for the determination of analyte 40. A tested liquid sample is first mixed (A) with antibody 38. If the analyte 40 is present in the tested sample, antibody 38 will bind to analyte 40 and will consequently be eliminated from the system. The mixture is then reacted with the probe. If no analyte 40 is present in the tested medium (B), there will be a maximum binding of antibodies 38 to immobilized antigens 36, and consequently a big increase in mass and a corresponding relatively big reduction in resonance frequency f'. Against this, where the liquid medium contains a large amount of analyte 40, all the antibodies 38 will be eliminated from the system, and there will be practically no change in the resonance frequency, which will remain essentially equal to $f_0$ (C).

Figure 4:
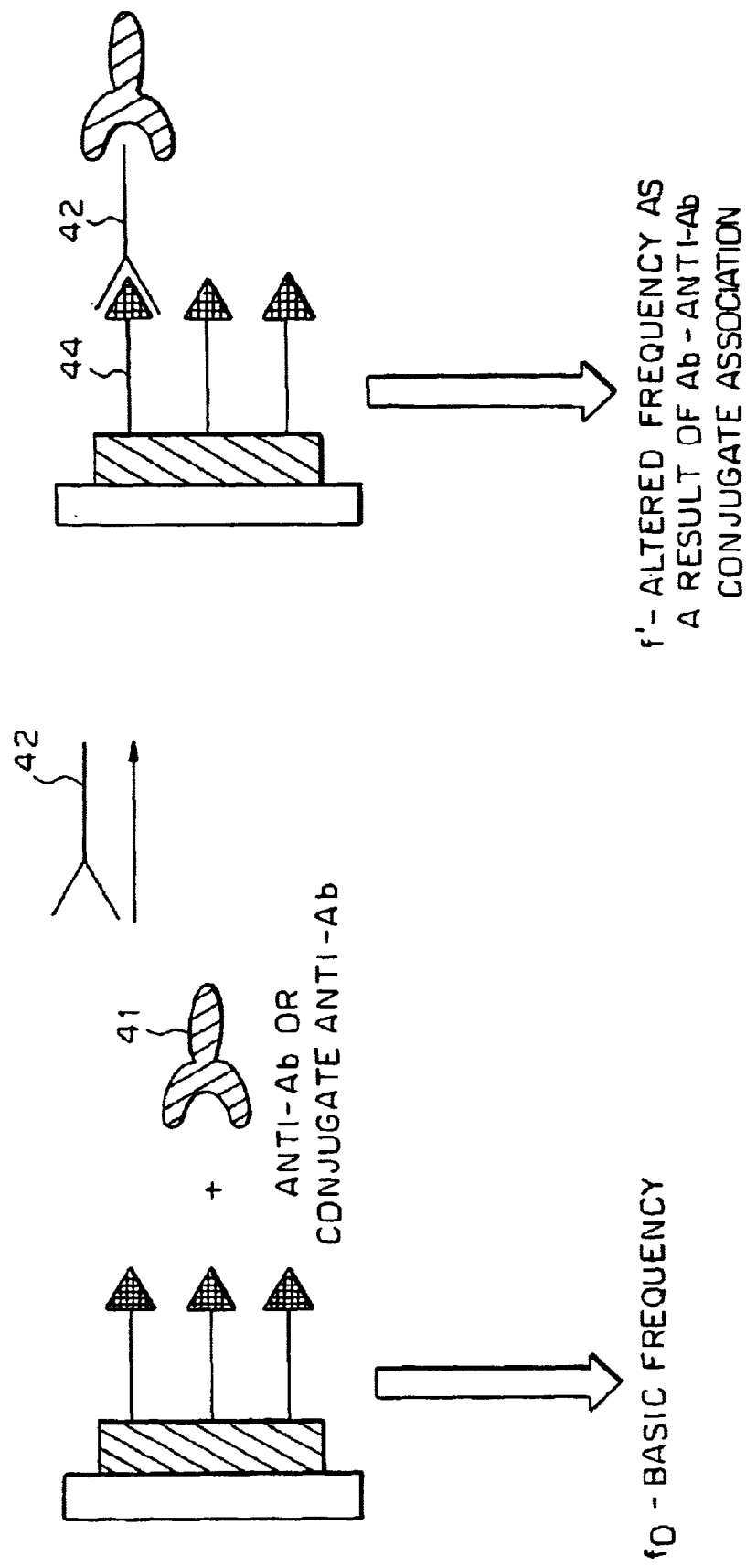
FIG. 4 shows a scheme for amplified QCM analysis of an Ab by the application of an anti-Ab or anti-Ab conjugate.

Reference is now made to FIG. 4, showing a scheme for an amplified QCM analysis of an analyte of a recognition pair. The scheme in this figure is essentially the same as in FIG. 1, the difference being the addition of amplifier group 41, which can bind to or complex with antibody 42. Amplifier group 41 functions to increase sensitivity of the system. After the antibody is allowed to bind to the immobilized antigens 44, or simultaneously therewith, group 41 is brought into contact with the sensing member, whereby it binds to the antibodies 42 bound to the immobilized antigens 44. Consequently, rather than a small Δf response, in this case there will be a much larger Δf response arising from the considerable increase of mass caused by group 41.

Figure 5:
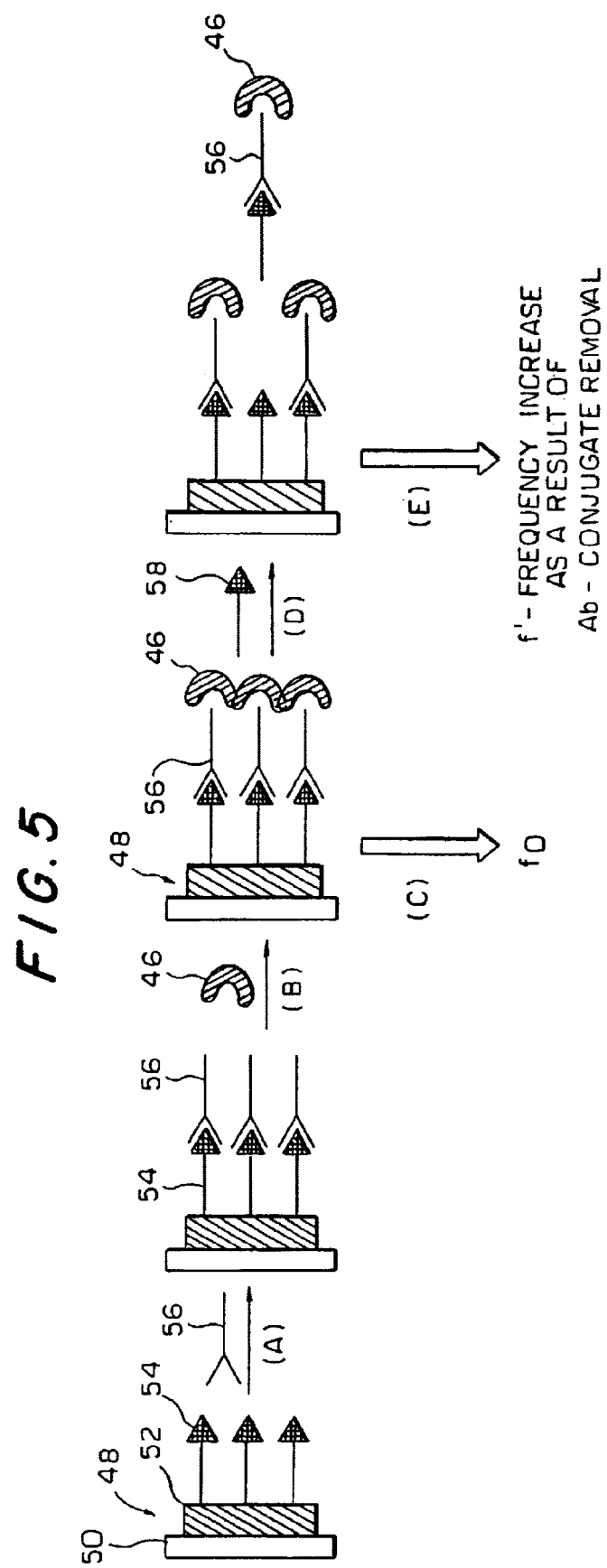
FIG. 5 shows an amplification of an antigen QCM analysis by the detachment of an Ab-conjugate complex from the QCM monolayer electrode.

FIG. 5 is an amplification version of the scheme shown in FIG. 2, making use of an amplifier group 46. The probe 48 comprises a piezoelectric crystal 50 with gold electrodes 52 having immobilized thereon antigens 54, which are one member of a recognition pair consisting also of antibodies 56. Probe 48 is challenged (A) with a solution comprising antibodies 56 in an amount to ensure that antibodies 56 will bind to immobilized antigens 54 saturating all possible binding sites. Group 46 is then added (B), which then binds to antibodies 56. Group 46 may, for example, be an antibody directed against antibodies 56. At this stage a first reading, $f_0$, is obtained (C) and then probe 48 is challenged with analyte 58 (D) which by a binding competition with immobilized antigen 54 brings to some release of complexes, consisting of antibodies 56 and group 46 from the probe. This will result in a relatively big mass reduction which will in turn result in a relatively big increase in resonance frequency (E).

The sensitivity of the system can be increased by creating large molecular complexes by means of complexation or conjugation. Examples are shown in FIG. 6. The basic configuration is a complex formed between an antibody 60 and an anti-antibody 61 shown in FIG. 6A. The sensitivity can be increased further by increasing the molecular complex mass, for example by binding or complexing to colloid particle 62 (FIG. 6B).

Another way to increase the molecular complex mass, shown in FIG. 6C, is to conjugate biotin molecules 63 to antibody 60, and then by reacting the conjugated antibody 64 with avidin molecule 65, a large complex 66 comprising mainly avidin molecule 65 and antibody 60 is formed. A further scheme, shown in FIG. 6D, is the complexation of avidin molecules in a similar fashion to the anti-antibody 61.

Figure 7:
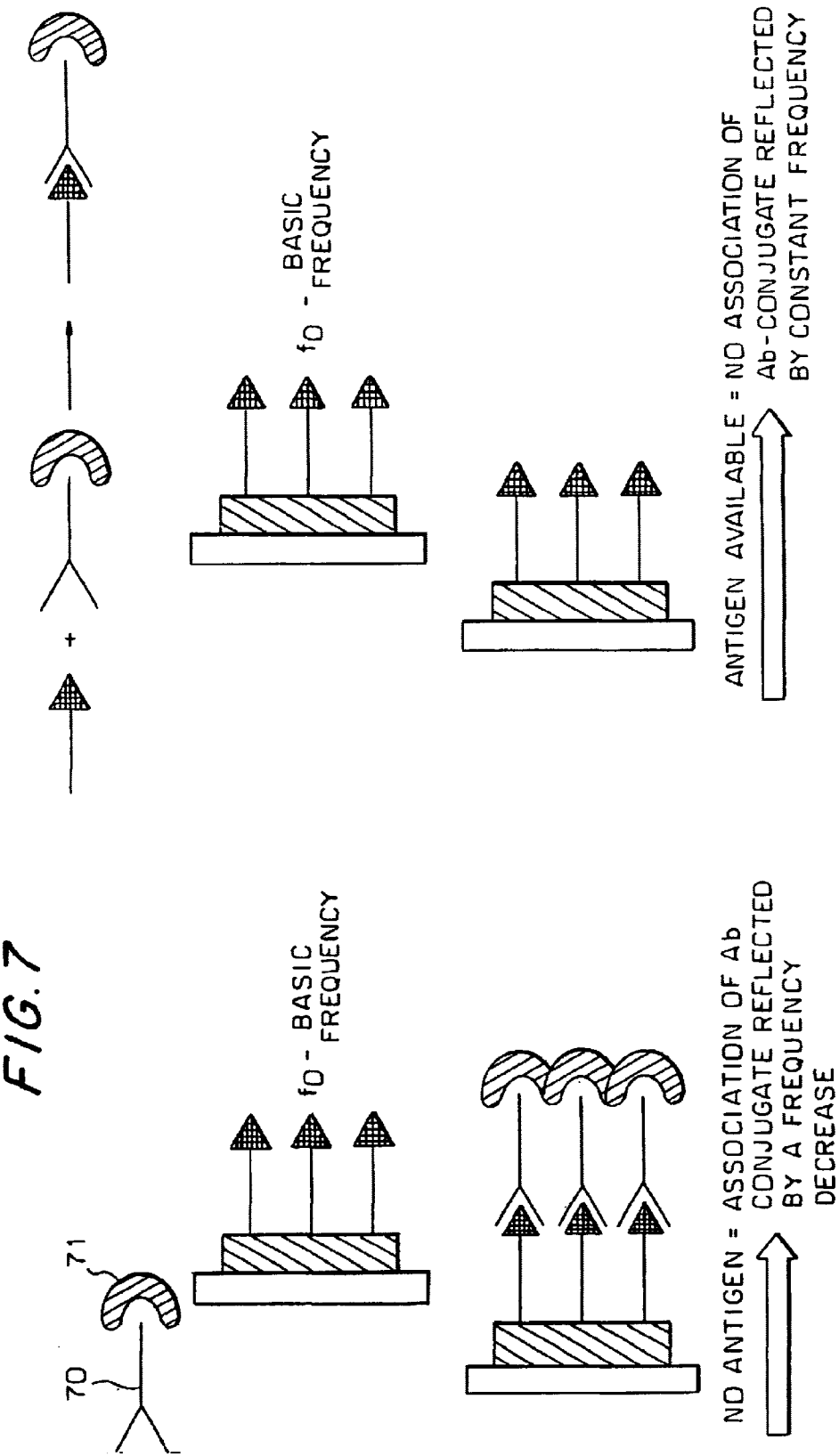
FIG. 7 shows an amplification of antigen QCM-analysis by treatment of an antigen monolayer QCM-probe with a mixture consisting of the antigen analyte and a fixed, predetermined, concentration of the Ab-conjugate complex.

FIG. 7 shows a system which is essentially similar to FIG. 3, with the addition of an amplifier group 71 bound to antibody 70. The manner of performing of the method is essentially the same as that of FIG. 3, and the reader is referred to the description relating to FIG. 3 for explanations.

Figure 8:
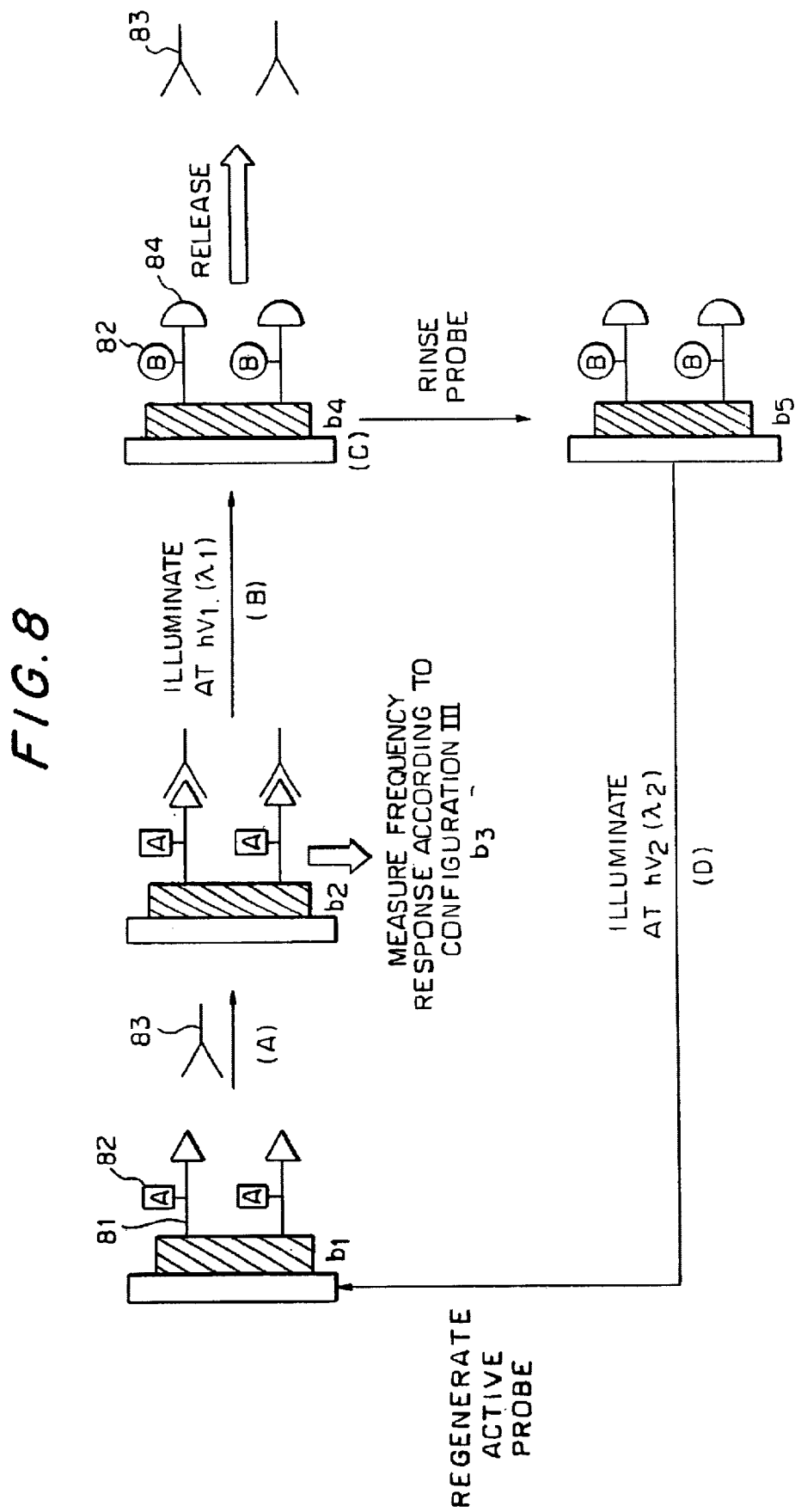
FIG. 8 shows the regeneration of the sensing member by light isomerization.

Reference is now being made to FIG. 8, which is a representation of another embodiment in accordance with the direct embodiment of the invention. This embodiment allows the regeneration of the probe after performance of the measurement for re-use in subsequent measurement. This feat is achieved, in accordance with this embodiment, by modifying the immobilized member 81 by isomerizable group 82 which has two states A and B, and is capable of switching reversibly between the two states by exposure to light of an energy $hv_1$ (having a wavelength $\lambda_1$) and energy $hv_2$ (having a wavelength $\lambda_2$). (This switching of the two states is show n schematically at the bottom of the figure.) The switching between the two isomerization states A and B causes a conformational change of the modified immobilized member which brings to a change in its affinity to binding to member 83 (in this case an antibody): in state A, the modified immobilized member is capable of binding member 83 with a high affinity; in state B, the affinity of binding to member 83 becomes very low.

The method of performance of the analyte determination (A) is essentially similar to FIG. 1 and the reader is referred to the description relating to this figure, the difference being that after finalizing the determination, the sensing member is illuminated by a light having a wavelength $\lambda_1$ (B), and consequently group 82 changes from state A to state B, which brings to a change in confirmation of immobilized member 81, which causes release of member 83. After rinsing (C), the electrode can be regenerated (D) by illumination with a light having a wavelength $\lambda_2$.

Figure 9C:
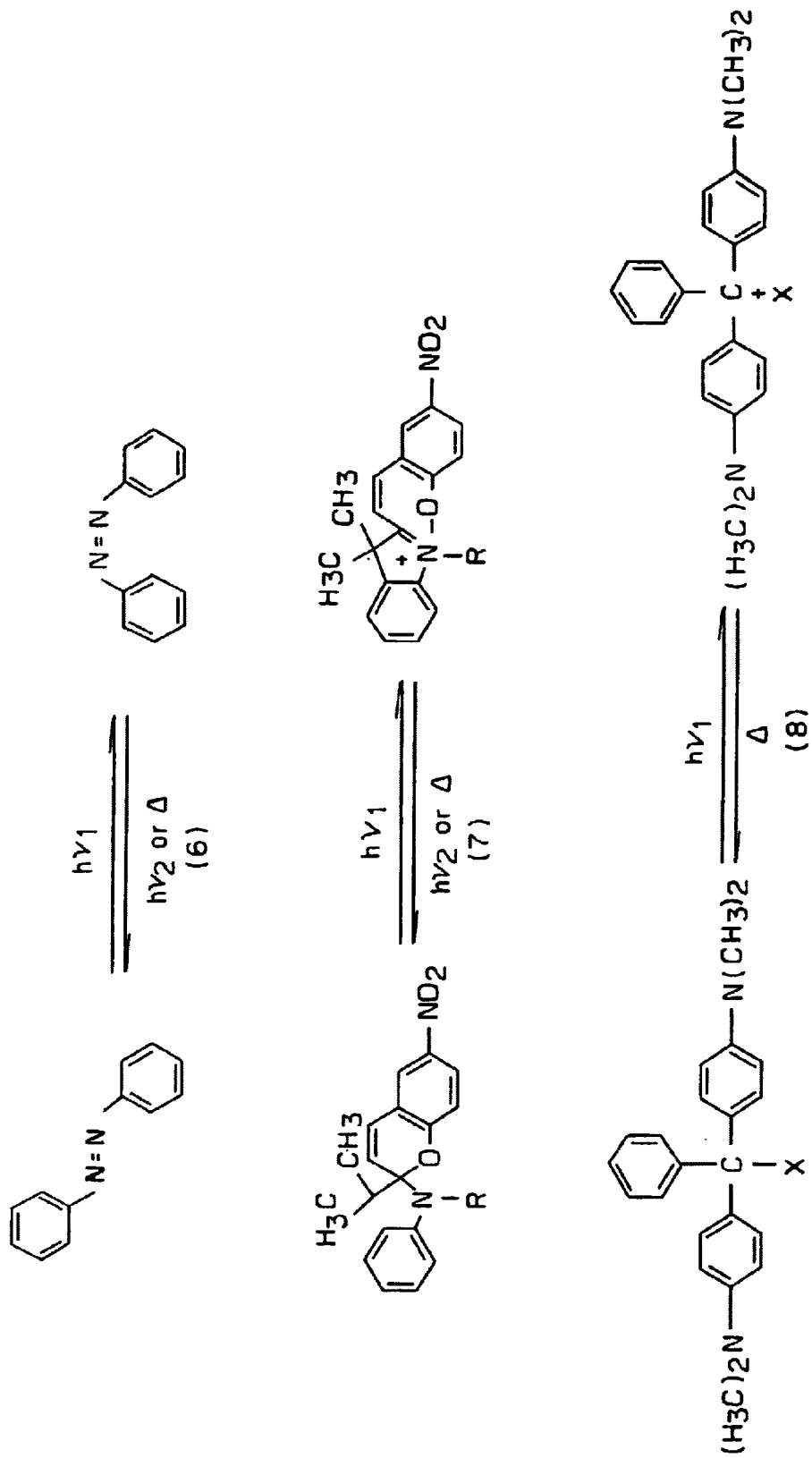
FIG. 9 shows formulae of photoisomerizable groups and some examples of photo-induced and heat treatment-induced conformational changes.

Examples of five families of compounds which could be used as said group can be seen in FIG. 9—structures (1) to (5) namely: azobenzenes (1), spiropyranes (2), fulgides (3), thiophenefulgides (4) or malachite green (5). Examples of the structural change in three of these five families of compounds which occurs upon their exposure to irradiation of light energy of an appropriate wavelength is illustrated by schemes (6) to (8) of FIG. 9. Specifically scheme (6) exemplifies azobenzenes, scheme (7) spiropyranes and scheme (8) malachite green. These compounds all require structural modification to prepare a group which can be linked to the member of a recognition pair to be immobilized on the surface of the electrode. Accordingly, in the preferred embodiment these compounds are modified chemically to form active esters, amine, carboxylic acid, or halide derivatives. The presence of such moieties facilitates linkage of the group to the immobilized member of the recognition pair. Scheme (9) illustrates both the appropriate wavelengths of light energy required to change spiropyran from a first state (A) to a second state (B) in which it is in its merocyanine form and also the structures of the first and second isomer states with (9B) and without (9A) the N-hydroxysuccinimide ester moiety.

Examples of photoisomerizable active esters which can be seen in FIG. 9 are N-hydroxyoxsuccinimide ester of N-propionic acid spiropyran (10), N-hydroxyoxsuccinimide ester of 4-carboxy azobenzene (11) and N-hydroxyoxsuccinimide, ester of thiophenefulgide (12).

The invention will now be illustrated further by a description of experiments conducted in accordance with the invention.

1. General 1.1 Piezocrystals and Experimental Set-Up

All measurements were performed using 9 MHz quartz piezocrystals (QPC) (AT cut type) covered with a layer (ca. 0.2 cm$^2$) consisting of sputtered gold (ca. 3000A) on a titanium (Ti) substrate (ca. 500 A) (Seiko EG&G). The frequency measurements were performed using a Quartz Crystal Analyzer (model QCA917, Seiko EG&G) linked to a personal computer.

Figure 10:
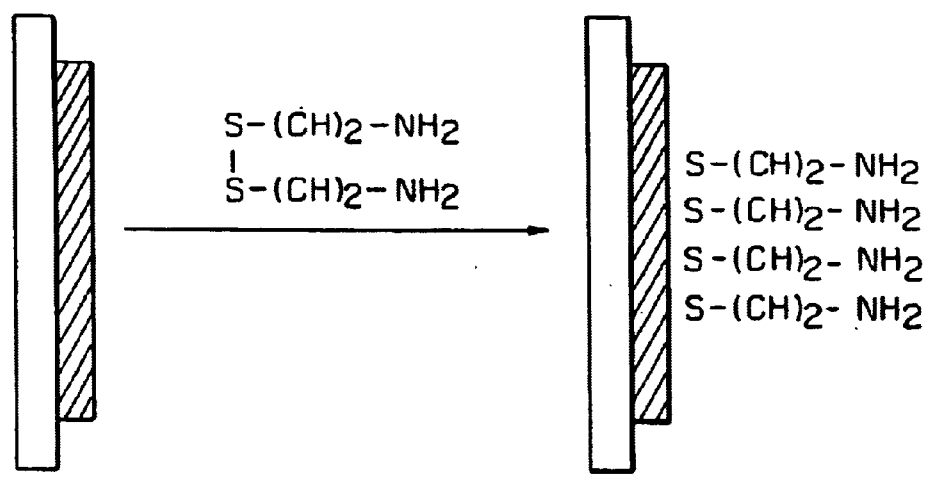
FIG. 10 shows the organization of cystamine monolayer on a QCM gold (Au) electrode.
Figure 11:
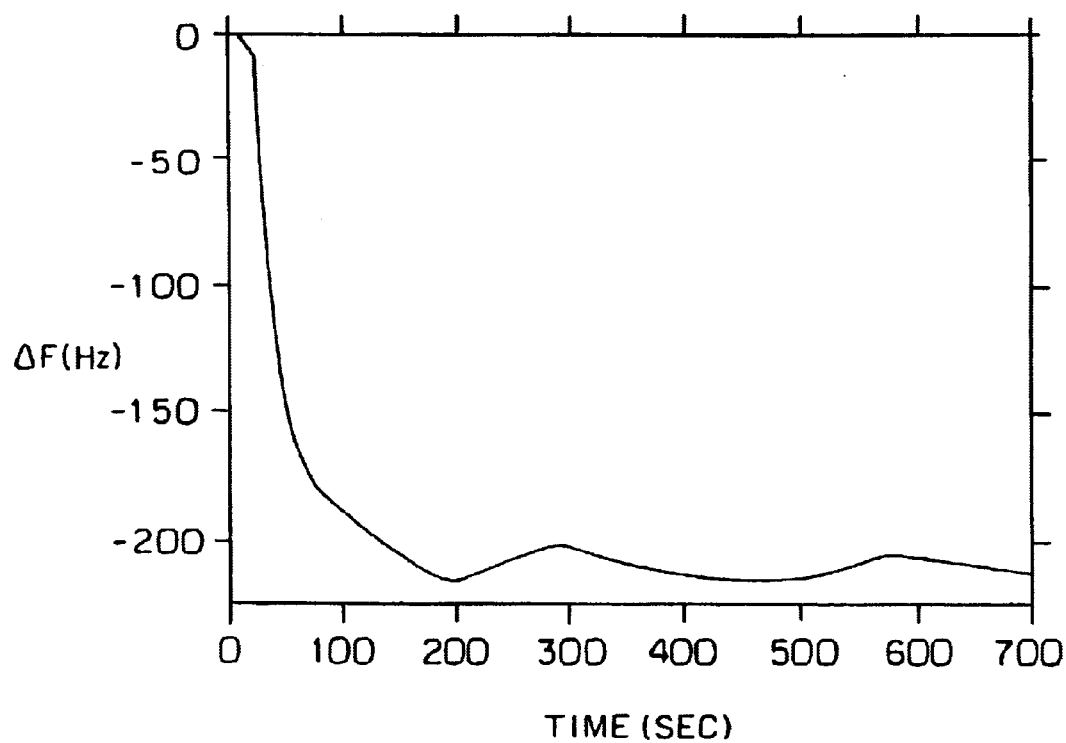
FIG. 11 shows a QCM-analysis of cystamine monolayer formation.

1.2 Primary Electrode Modification by a Functionalized Monolayer for Antigen or Antibody Attachment. Specific Example—Modification of Au-quartz Crystal by a Cystamine Monolayer The primary step for the organization of the sensing piezoelectric crystal involves the modification of the Au-electrode crystal by a functionalized thiolate monolayer that enables subsequent linkage of an antigen-Ab complex to the monolayer. Among the various possible functionalized monolayers (amine, carboxyl, hydroxy, diazonium) the organization of a cystamine monolayer is exemplified in FIG. 9. Quartz piezocrystal (QPC) was soaked in a solution of 0.2 M cystamine in water for 2 h. The frequency change during the cystamine adsorption on the electrode was a tool to detect the cystamine deposition, FIG. 10. The electrode was then rinsed thoroughly with water to remove the physically adsorbed cystamine. The frequency after the electrode rinsing was not altered as compared to the final value obtained during the adsorption process. That is, the cystamine molecules are strongly linked to the electrode surface. The observed frequency change $\Delta f$=−200 Hz (minus reflects frequency decrease) corresponds to the mass density of cystamine on the electrode corresponding to $1.16 \times 10^{-6}$ g·cm$^{-2}$ or ca. $5.2 \times 10^{-9}$ mol·cm$^{-2}$ (the densities are calculated using a geometrical area of the electrode).

Figure 12:
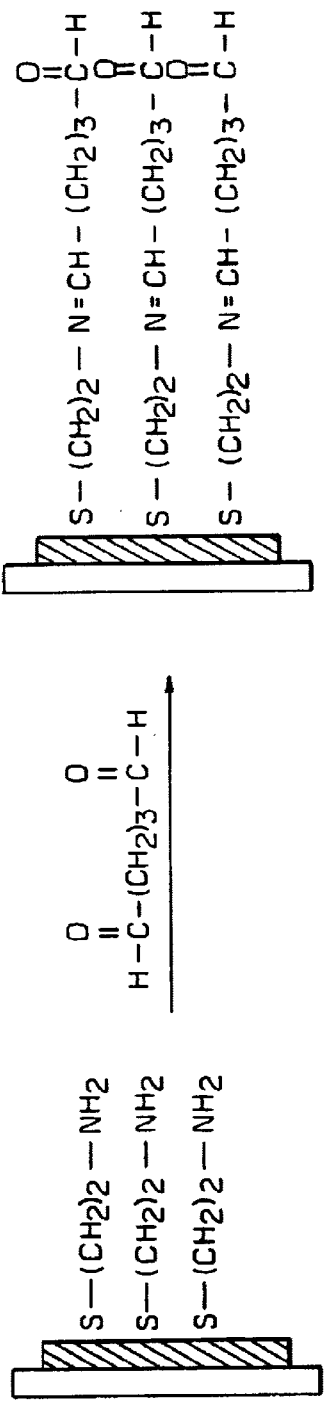
FIG. 12 shows the activation of the QCM-monolayer electrode by glutardialdehyde.
Figure 13:
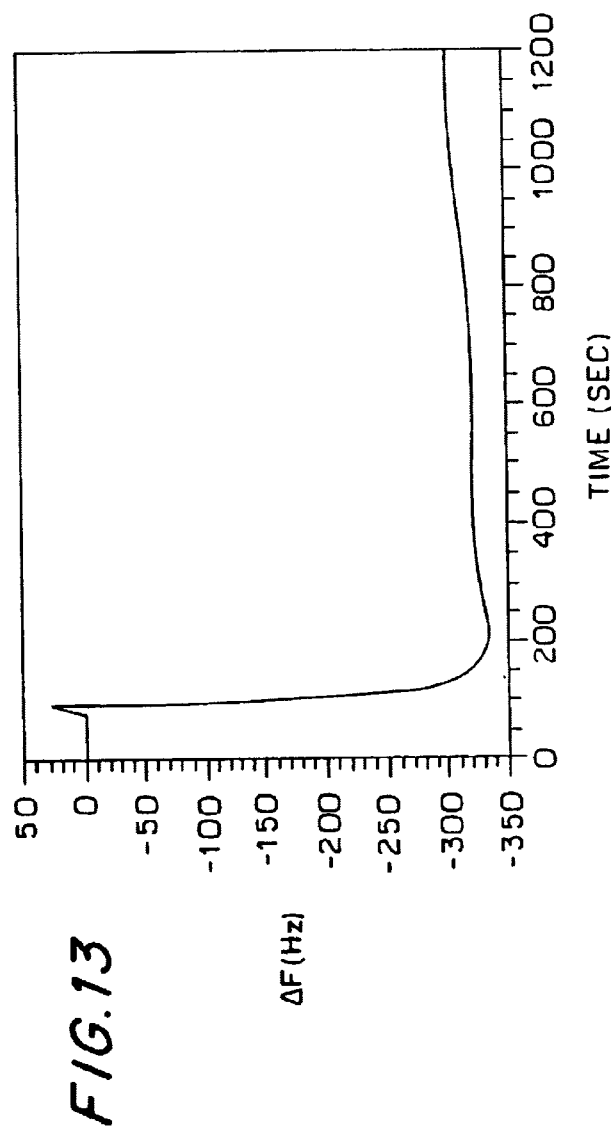
FIG. 13 shows QCM-analysis of the glutardialdehyde monolayer formation.
Figure 14:
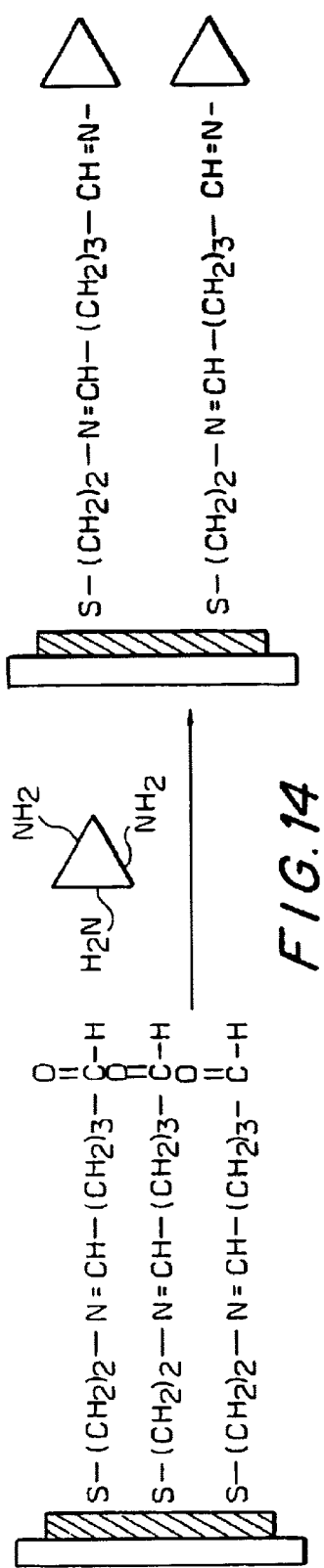
FIG. 14 shows the organization of HIV-1 antigen peptide on QCM Au-electrode.
Figure 15:
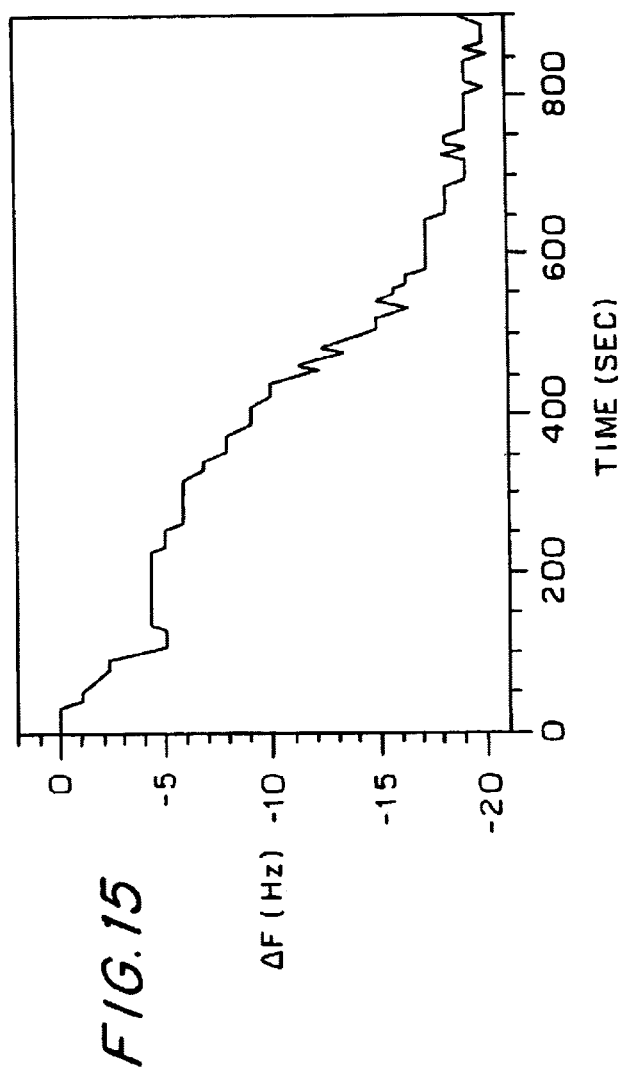
FIG. 15 shows QCM-analysis of a 3000-titer serum of HIV-1 Ab.

2. Experimental Results 2.1 QCM Detection of HIV-1 Antibody Using an Electrode Modified with HIV-Peptide Antigen An Au electrode modified with a primary cystamine monolayer was activated with glutaric dialdehyde (FIG. 12). The reaction was performed by treatment of the crystal in the QCM-cell with a 5% (v/v) glutaric dialdehyde solution in water for 20 min. at room temperature and following the frequency changes of the crystal during the reaction. (FIG. 13). The value $\Delta f$=−300 Hz corresponds to an electrode coverage of the electrode with glutaric dialdehyde of ca. $1.5 \times 10^{-8}$ mol·cm$^{-2}$. The resulting modified electrode was used for covalent immobilization of the HIV antigen (FIG. 14). The reaction was carried out by treatment of the crystal at room temperature in 0.01 M phosphate buffer, pH 7.4, containing 0.1 M NaCl and 0.4 mg·ml$^{-1}$ HIV-antigen for 12 hours. The immobilization was monitored by measuring the frequency of the modified crystal. The final frequency change was $\Delta f$=−140 Hz that yields a density of the immobilized HIV-antigen that corresponds to $6.4 \times 10^{-11}$ mol·cm$^{-2}$. The electrode modified with the antigen was used for detection of HIV-1 antibody (FIG. 15). A frequency change of $\Delta f$=18 Hz after 10 minutes is observed for an HIV-1 sample with a titer corresponding to 3000.

Figure 16:
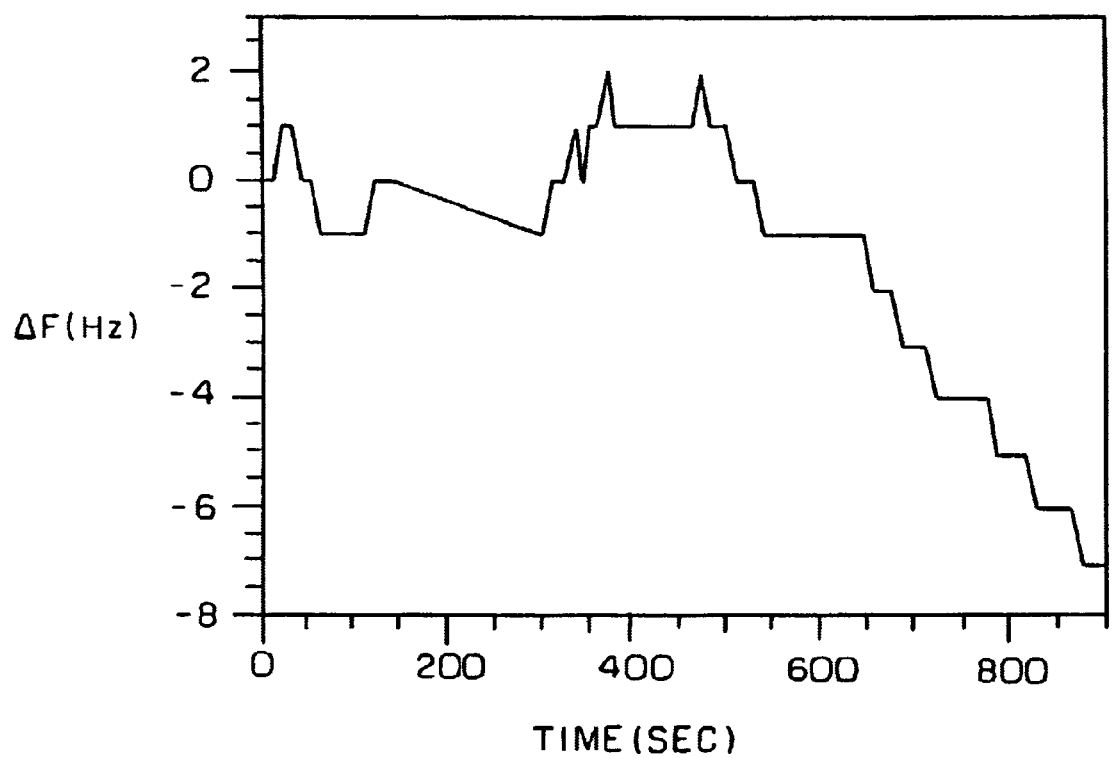
FIG. 16 shows QCM-analysis of goat serum (titer 80) by the HIV-1 antigen electrode.

The specifity of HIV-Ab detection was examined by treatment of the antigen electrode with goat serum (titer 80). A frequency decrease of only 2 Hz was observed after 10 minutes as a result of non-specific adsorption (FIG. 16). At lower measurement time intervals (4 minutes) the HIV-Ab causes a frequency change of $\Delta f$=15 Hz where the BSA control sample does not stimulate any detectable frequency change in the crystal frequency.

2.2 A Dinitrophenol Antigen Monolayer QCM-Electrode for Analysis of DNP-Ab

Figure 17:
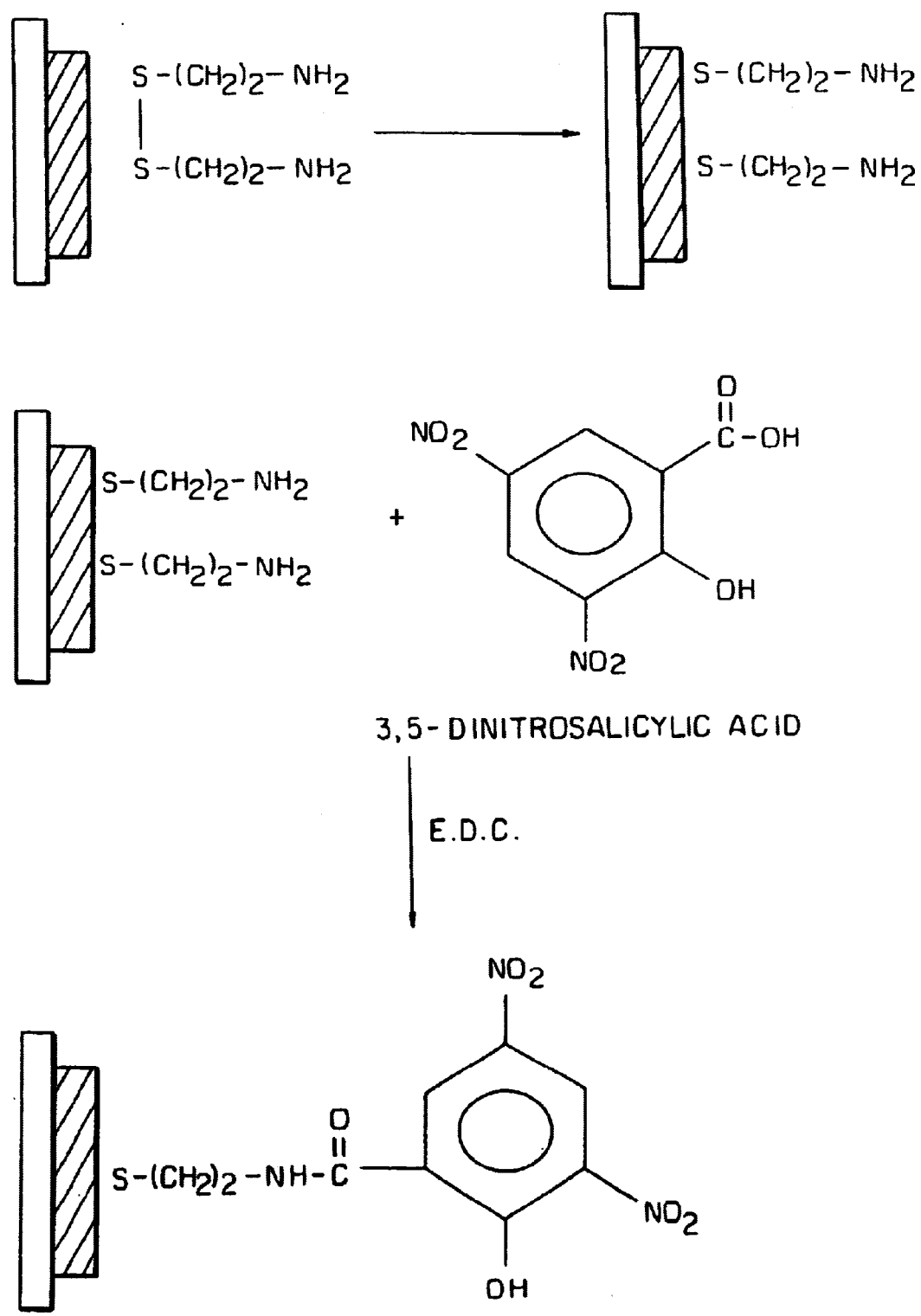
FIG. 17 shows the organization of a dinitrophenyl monolayer QCM electrode.

A cystamine Au-modified electrode was obtained as described under 2.1. The modified QCM-electrode was treated with a solution of 0.2 M 3,5-dinitrosalicylic acid, N-hydroxy-sulfosuccinimide sodium salt (as a promoter) and 1-ethyl-3-(3-dinitromethylaminoporpyl)carbodiimide (EDC) as a coupling reagent in 0.05 M HEPES buffer, pH=7.3, to generate the dinitrophenol antigen monolayer on the surface (FIG. 17). The reaction was carried out for 2 h at room temperature. The frequency change of the crystal as a result of coupling of 3,5-dinitrosalicylic acid was −90 Hz, corresponding to an antigen coverage of $1.3 \times 10^{-12}$ mol·cm$^{-2}$.

Figure 18:
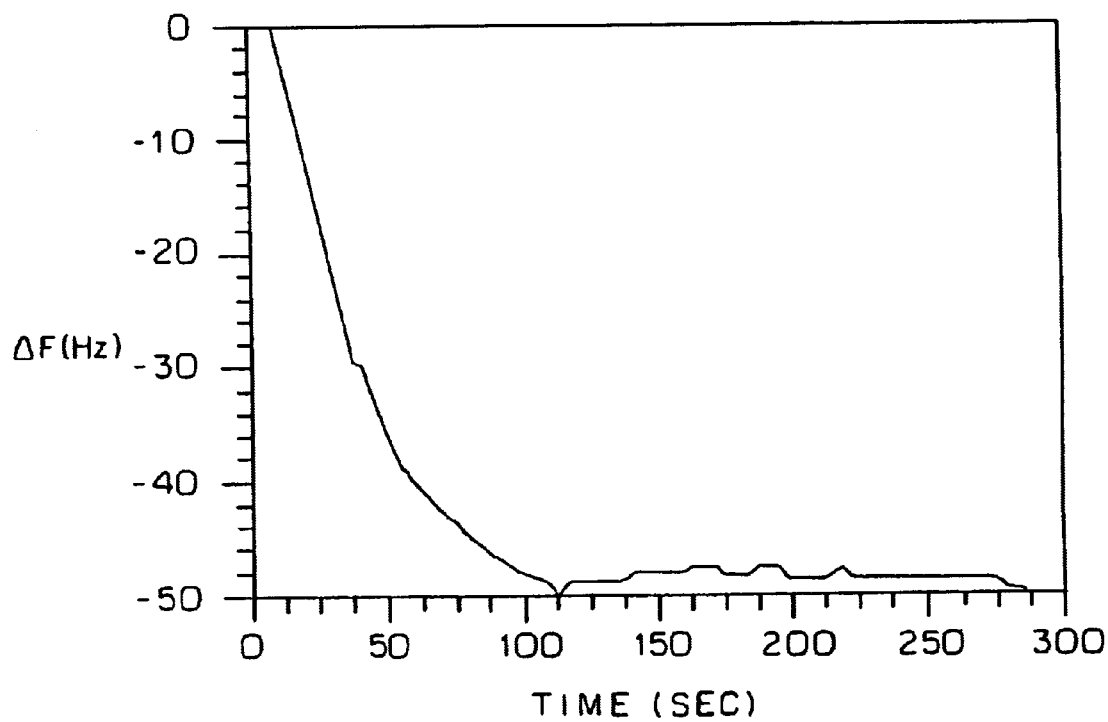
FIG. 18 shows a QCM-analysis of anti-DNP-Ab by dinitrophenyl antigen monolayer QCM electrode.

The antigen QCM electrode was challenged with a DNP-Ab solution $1.4 \times 10^{-11}$ M. A frequency change of $\Delta f$=−30 Hz was observed after 800 seconds, indicating the adsorption of DNP-Ab to the crystal (FIG. 18).

Figure 19:
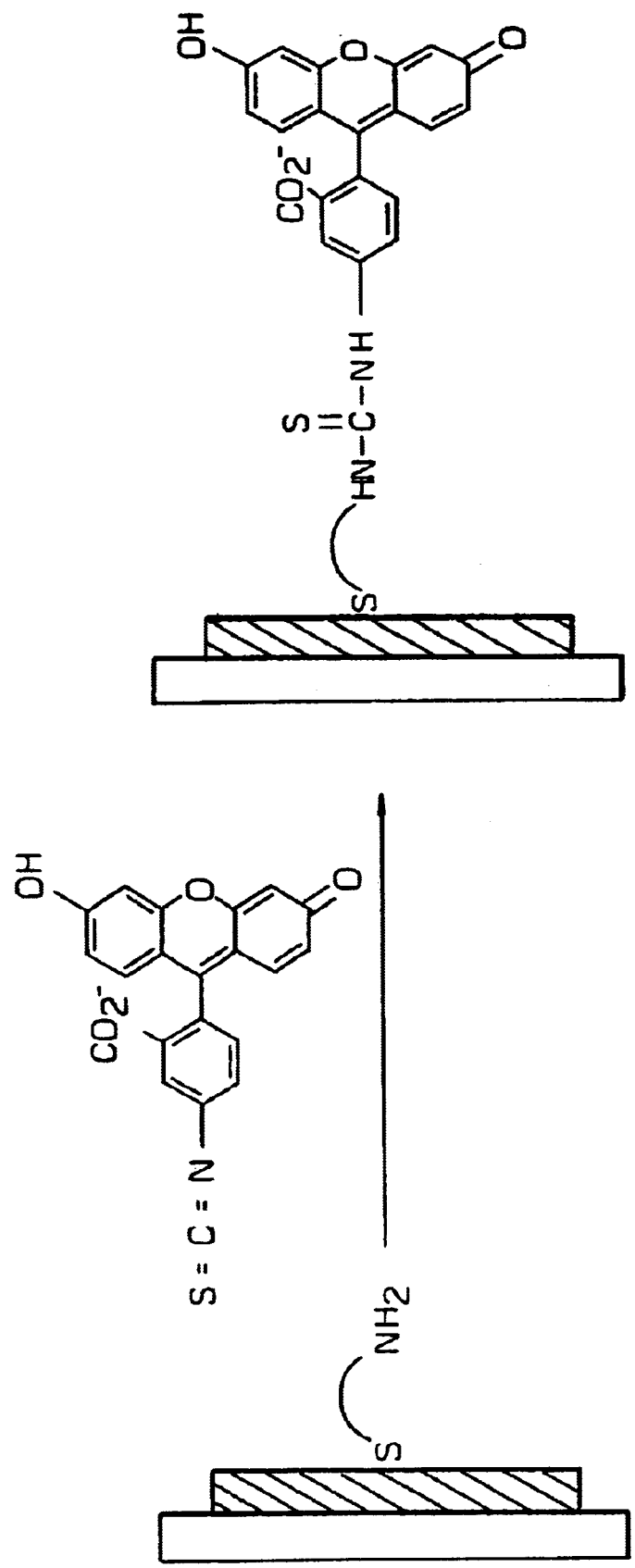
FIG. 19 shows organization of a fluorescein antigen monolayer QCM-electrode.

2.3 A Fluorescein Antigen Monolayer QCM-Electrode for Analysis of Anti-Fluorescein A cystamine Au-modified electrode was obtained as described under 2.1. The modified electrode was reacted with fluorescein isothiocyanate to generate the antigen monolayer electrode (FIG. 19). Upon treatment of the electrode with antifluorescein Ab, $1 \times 10^{-6}$ mg·ml$^{-1}$, a frequency change of $\Delta f$=−60 Hz was observed.

Figure 20:
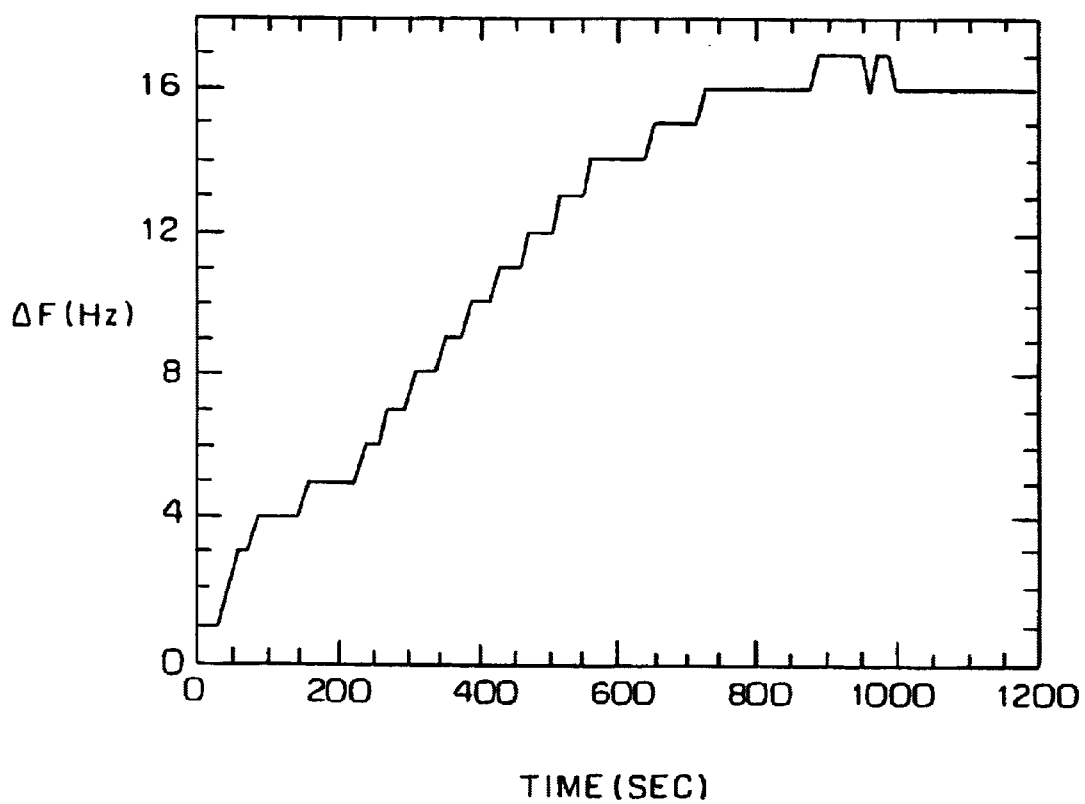
FIG. 20 shows QCM-analysis of 2,4-dinitrophenol, $1.4 \times 10^{-7}$ g·ml$^{-1}$, by detachment of DNP-Ab from the antigen-DNP-Ab monolayer electrode.

2.4 Dinitrophenol Antigen Monolayer Electrode with Bound DNP-Ab for 2,4 Dinitrophenol Analysis in a Sample According to the Configuration Shown in FIG. 2, Where Displacement of the Antibody Pre-Immobilized on the Antigen Monolayer Electrode Surface is Used for Detection of an Antigen in a Sample A cystamine Au-modified electrode was obtained as described under 2.1. A solution of 0.2 M 3,5-dinitrosalicylic acid, N-hydroxysulfosuccinimide sodium salt (as a promoter) and 1-ethyl-3-(3-dinitromethylaminopropyl) carbodiimide (EDC) (as a coupling reagent) in 0.05 M HEPES buffer, pH 7.3, was used for further modification of the electrode surface with dinitrophenol units (FIG. 17). The reaction was performed for 2 h at room temperature and the final frequency change due to immobilization of 3,5-dinitrosalicylic acid was ca. −90 Hz, corresponding to an antigen coverage of $2.5 \times 10^{-9}$ mol·cm$^{-2}$. This antigen monolayer-modified electrode was used for specific adsorption of dinitrophenol antibody (monoclonal mouse IgE anti-DNP). The frequency change of the crystal as a result of Ab-binding was monitored again (similarly to FIG. 18). The final frequency change of $\Delta f$=−50 Hz resulted from the antibody deposition and gives the surface density of the antibody as ca. $1.93 \times 10^{-7}$ g·cm$^{-2}$. The antigen/antibody modified electrode was treated with an analyte sample aqueous solution containing $1.4 \times 10^{-7}$ g·ml$^{-1}$ 2,4-dinitrophenol (DNP) and the frequency change, resulting from the antibody desorption was recorded (FIG. 20). The displacement of the antibody was induced by its reaction with a new available antigen (DNP) being in the solution.

2.5 Determination of 2,4-Dinitrophenol by Interaction with a Predetermined Concentration of DNP-Ab and Analysis of the Mixture with the Antigen Monolayer Crystal According to the Configuration of FIG. 3

The electrode was modified with 3,5-dinitrosalicylic acid as described under 2.2. This electrode was treated with an aqueous mixture that contains the sample analyte, 2,4-dinitrophenol, $1.4 \times 10^{-11}$ M and a predetermined DNP-Ab concentration of $1.4 \times 10^{-1}$ M. The final frequency change of the crystal was $\Delta f=7$ Hz after 800 seconds of interaction. For comparison treatment of the electrode with a sample that lacks 2,4-dinitrophenol but includes the predetermined DNP-Ab concentration, $1.85 \times 10^{-11}$ M, results in a frequency change of $\Delta f=30$ Hz after 800 seconds of interaction.

2.6 Amplification of 2,4-Dinitrophenol Analysis by an Antigen-DNP-Ab-Biotinavidin Complex Associated with the Quartz Electrode According to the Configuration Shown in FIG. 5

2.6.1. Preparation of Biotin Modified DNP-Ab

The 0.02 M DNP-antibody solution in 0.1 M phosphate buffer, pH 7.2 was reacted with 0.02 M biotin amidocaproate N-hydroxysuccinimide ester for 3 h at 25° C. The reaction mixture was dialyzed overnight at 4° C. against a 0.01 M phosphate buffer, pH 7.4, and the purified DNP-antibody-biotin was used to assemble the antigen-Ab-conjugate complex on the crystal electrode.

Figure 21:
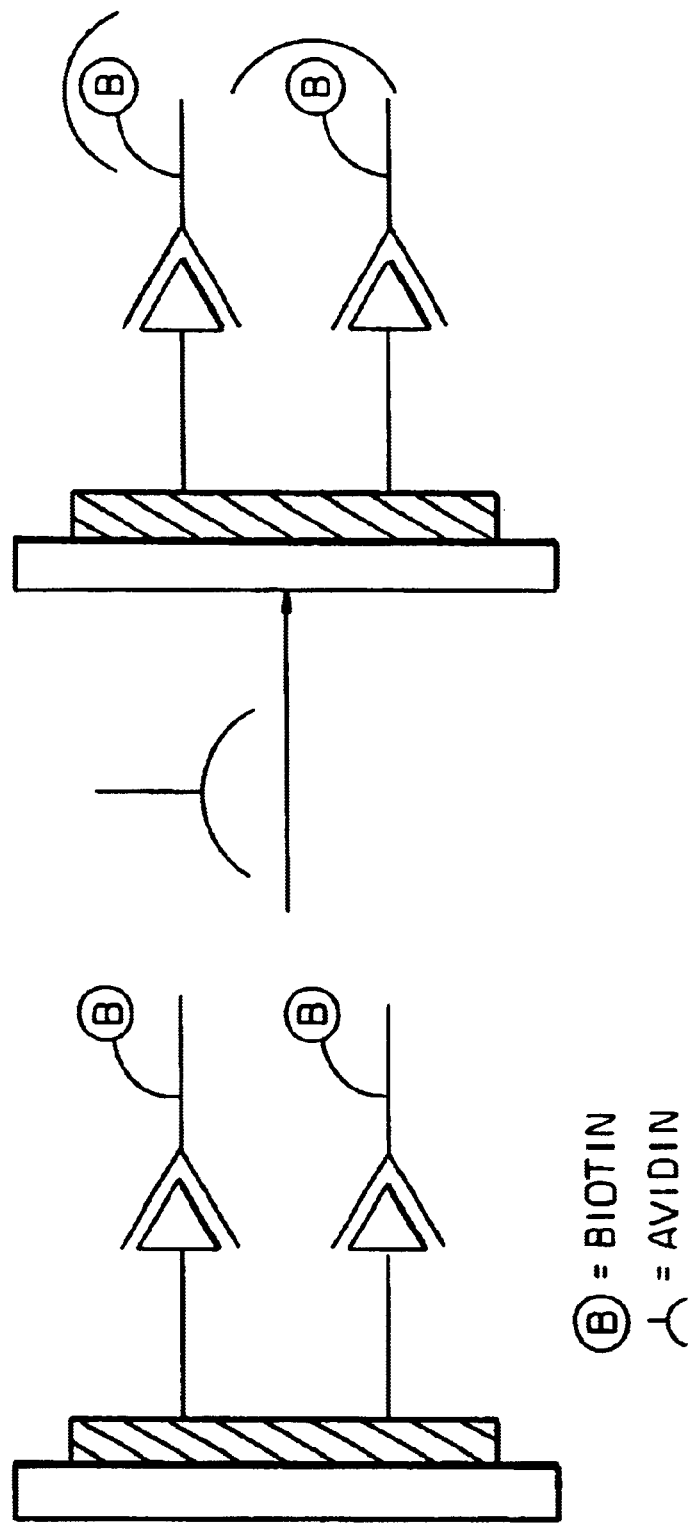
FIG. 21 shows the assembly of the dinitrophenyl antigen-DNP-biotin-avidin conjugate complex on a QCM-electrode.

2.6.2 Construction of an Antigen-DNP-Ab-Biotin-Avidin Complex on the QCM Electrode The antigen-Ab-conjugate complex was assembled onto the crystal electrode as outlined in FIG. 21. An electrode that included a dinitrosalicylic acid monolayer was prepared as described under 2.2. The monolayer-modified crystal was treated with a solution of biotin-modified DNP-Ab, 1.25 mg·ml$^{-1}$. Adsorption of the modified Ab to the monolayer antigen induces frequency change of $\Delta f=-50$ Hz indicating a surface coverage by the Ab corresponding to $1.8 \times 10^{-12}$ mol·cm$^{-2}$. The resulting antigen-DNP-Ab-biotin monolayer electrode was treated with avidin solution, 1.0 mg·ml$^{-1}$. The resulting frequency change after 5 minutes as a result of formation of the biotin-avidin complex is $\Delta f=-120$ Hz which corresponds to a surface coverage of $5.5 \times 10^{-12}$ mol·cm$^{-2}$ with the avidin complex.

3. Analysis of 2,4-Dinitrophenol by the Antigen-DNP-Ab-Conjugate Complex QCM Electrode, According to the Configuration Shown in FIG. 5

Figure 22:
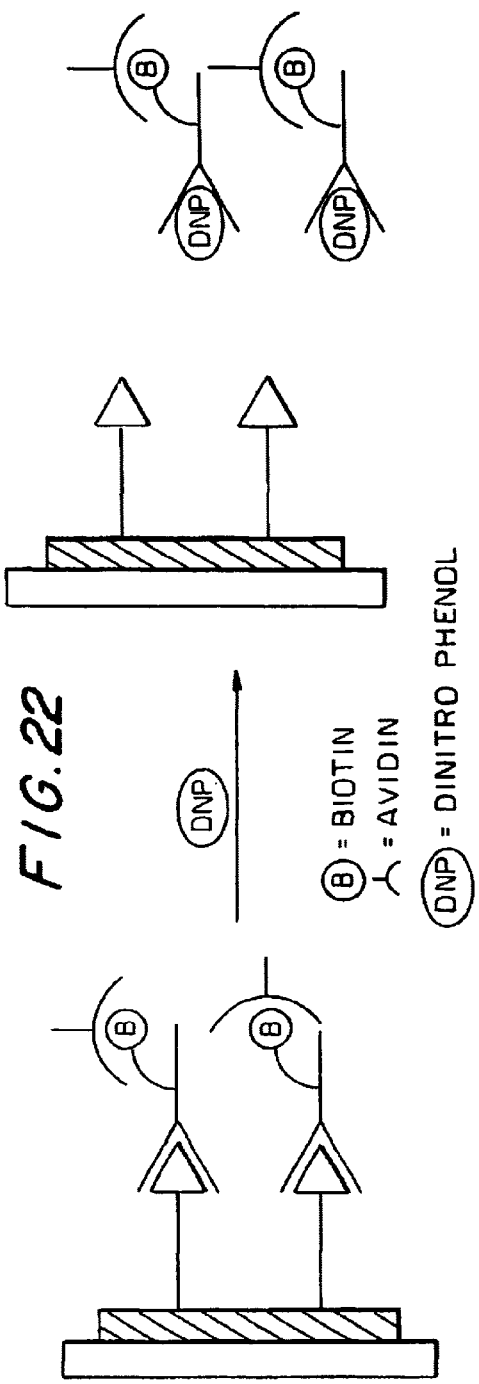
FIG. 22 shows a scheme of QCM analysis of a sample solution that contains 2,4-dinitrophenol (DNP) by displacement of the dinitrophenyl antigen-DNP-biotin-avidin conjugate complex associated with a QCM electrode.
Figure 23:
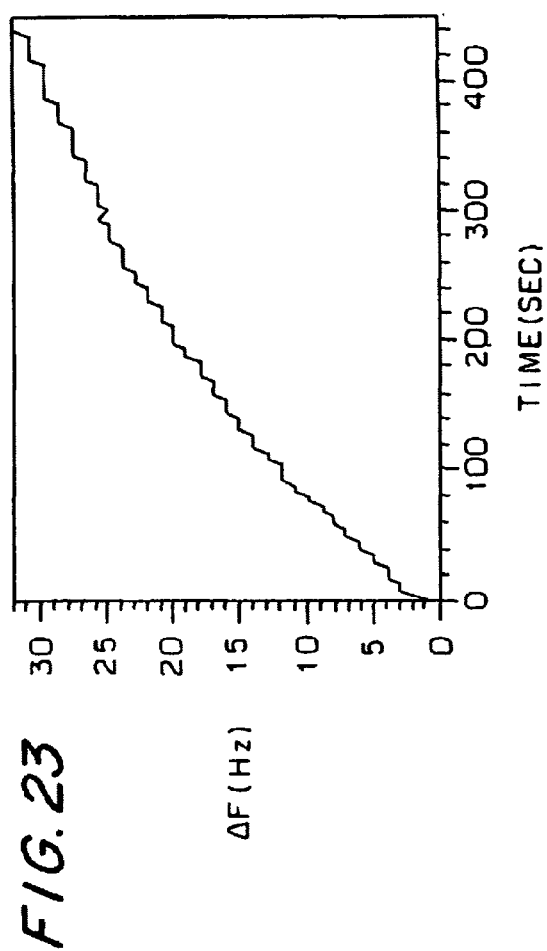
FIG. 23 shows the $\Delta f$ response in the system of FIG. 22 following exposure to $2.7 \times 10^{-8}$ g·ml$^{-1}$ of DNP.

The antigen-DNP-Ab-biotin-avidin complex QCM electrode was treated with a 2,4-dinitrophenol solution, $2.7 \times 10^{-8}$ g·ml$^{-1}$. The caused dissociation of the DNP-Ab complex conjugate from the electrode by the analyte antigen, as illustrated in FIG. 22, which was followed by the frequency changes of the crystal. A frequency change of $\Delta f=30$ Hz is observed after 400 seconds of interaction (FIG. 23).

What is claimed is:

1. A system for determining binding between a first and a second member of a recognition pair, said recognition pair being a pair selected from the group consisting of antigen-antibody, ligand-receptor, sugar-lectin, biotin-avidin, enzyme-substrate, oligonucleotide-oligonucleotide with a complementary sequence, oligonucleotide-protein, and oligonucleotide-cell, the system comprising:

(a) a probe comprising a piezoelectric crystal, electrodes on two opposite faces of said crystal, and one or more metal plates carried on the surface of said crystal, said metal plates being the same or different than said electrodes and having immobilized thereon by chemical association, chemical attachment or chemisorption a monolayer comprising said first member of a recognition pair, wherein binding of said second member of the recognition pair to said immobilized first member, or dissociation of a prior bound recognition pair and release of said second member from said probe, causes a change of mass resulting in a change in the resonance frequency of said probe;

(b) a vessel for holding a liquid, wherein said probe is immersed in said liquid to allow either
  binding between said immobilized first member and a second member dissolved in said liquid, or
  release of said second member bound to said first member in a prior bound recognition pair, into said liquid; and (c) an electric or electronic circuitry for generating an alternating electric field between said electrodes, for measuring the resonance frequency of said crystal, and for determining a change in the resonance frequency of said probe and deducing therefrom the occurrence of either binding between said immobilized first member and a dissolved second member or release of said second member, bound to said immobilized first member in a prior bound recognition pair, into said liquid, wherein said immobilized first member is immobilized on a surface of said metal plates by means of a linking group, having the following general formula (I):

$$Z-R^1-Q \qquad (I)$$

wherein:

Z represents a sulphur-containing moiety which chemically associates with, attaches to, or chemisorbs onto the surface of said metal plates;

$R^1$ represents a connecting group;

Q is a functional group which forms a covalent bond with a moiety of said immobilized first member of said recognition pair.

2. A system for determining binding between a first and a second member of a recognition pair, said recognition pair being a pair selected from the group consisting of antigen-antibody, ligand-receptor, sugar-lectin, biotin-avidin, enzyme-substrate, oligonucleotide-oligonucleotide with a complementary sequence, oligonucleotide-protein, and oligonucleotide-cell, the system comprising:

(a) a probe comprising a piezoelectric crystal, electrodes on two opposite faces of said crystal, and one or more metal plates carried on the surface of said crystal, said metal plates being the same or different than said electrodes and having immobilized thereon by chemical association, chemical attachment or chemisorption a monolayer comprising said first member of a recognition pair, wherein binding of said second member of the recognition pair to said immobilized first member, or dissociation of a prior bound recognition pair and release of said second member from said probe, causes a change of mass resulting in a change in the resonance frequency of said probe;

(b) a vessel for holding a liquid, wherein said probe is immersed in said liquid to allow either
  binding between said immobilized first member and a second member dissolved in said liquid, or
  release of said second member bound to said first member in a prior bound recognition pair, into said liquid; and (c) an electric or electronic circuitry for generating an alternating electric field between said electrodes, for measuring the resonance frequency of said crystal, and for determining a change in the resonance frequency of said probe and deducing therefrom the occurrence of either binding between said immobilized first member and a dissolved second member or release of said second member, bound to said immobilized first member in a prior bound recognition pair, into said liquid, wherein said immobilized first member has or is linked to an isomerizable group which changes its isomerization state as a result of exposure to energy, said isomerizable group having a first and a second isomerization state and converts from said first state to said second state by exposure to a first energy type and from said second state to said first state upon exposure to a second energy type, wherein, in said first state, said immobilized first member has a high affinity of binding to said second member, and in said second state, said immobilized first member has a low affinity of binding to said second member.

3. The system according to claim 2, wherein said first energy type is light irradiation of a first wavelength and said second energy type is light irradiation of a second wavelength, said light irradiation being in the infrared, visible light or ultraviolet range.

4. The system according to claim 2, wherein one of said first or said second energy type is light irradiation in the infrared, visible light or ultraviolet range, and the other of said first or said second type is a mild thermal treatment.

5. A method for determining an analyte in a liquid medium, comprising the steps of:
(a) providing a probe comprising a piezoelectric crystal, electrodes on two opposite faces of said probe, and one or more metal plates carried on the surface of said crystal, said metal plates being the same or different than said electrodes and having immobilized thereon by chemical association, chemical attachment or chemisorption a monolayer comprising a first member of a recognition pair, said recognition pair being selected from the group consisting of antigen-antibody, ligand-receptor, sugar-lectin, biotin-avidin, enzyme-substrate, oligonucleotide-oligonucleotide with a complementary sequence, oligonucleotide-protein, and oligonucleotide-cell, said second member of said recognition pair being non-covalently bound to said immobilized first member, said second member binding to an analyte, wherein the binding between said second member and said analyte is competitive with the binding of said second member to said immobilized first member;
(b) measuring an initial resonance frequency of said probe;
(c) contacting said probe with a liquid medium under conditions and for an amount of time such that, in the presence of said analyte in said liquid medium, at least some of said second member non-covalently bound to said first member will be released and bind to said analyte; and
(d) measuring a second resonance frequency, whereby a higher second resonance frequency as compared to the initial resonance frequency, which results from a decrease in mass of said probe, as a consequence of release of said second member into said liquid medium, indicates the presence of said analyte in said liquid medium.

6. The method according to claim 5, wherein said analyze is a molecule suspended or dissolved in a gas, the method further comprising the step of passing a gas containing a sample of suspended or dissolved molecules through a liquid to determine the presence of said analyte in the liquid.

7. The method according to claim 5, wherein said immobilized first member is immobilized on a surface of said metal plate by a linking group, having the following general formula (I):

Z—R¹Q (I)

wherein:
Z represents a sulphur-containing moiety which chemically associates with, attaches to, or chemisorbs onto the surface of said metal plate;
R¹ represents a connecting group;
Q is a functional group which forms a covalent bond with a moiety of said first member of said recognition pair.

8. The method according to claim 5, wherein said immobilized first member has or is linked to a group which changes its isomerization state as a result of exposure to energy, said group having a first and a second isomerization state and converts from said first state to said second state upon exposure to a first energy type and from said second state to said first state upon exposure to a second energy type, wherein, in said first state, said immobilized first member has a high affinity of binding to said second member, and in said second state, said immobilized first member has a low affinity of binding to said second member.

9. A method for determining binding between a first member of a recognition pair and a second member of a recognition pair, said recognition pair being a pair selected from the group consisting of antigen-antibody, ligand-receptor, sugar-pectin, biotin-avidin, enzyme-substrate, oligonucleotide-oligonucleotide with a complementary sequence, oligonucleotide-protein, and oligonucleotide-cell, said second member being initially contained in a liquid medium, comprising the steps of:
(a) providing a probe comprising a piezoelectric crystal, electrodes on two opposite faces of said crystal, and one or more metal plates carried on the surface of said crystal, said metal plates being the same or different than said electrodes and having immobilized thereon by chemical association, chemical attachment or chemisorption a monolayer comprising said first member of said recognition pair;
(b) measuring an initial resonance frequency of said probe;
(c) contacting said probe with a liquid medium containing said second member for an amount of time sufficient to allow binding between said first member and said second member; and
(d) measuring a second resonance frequency, whereby a lower second resonance frequency, as compared to the initial resonance frequency, which results from an increase in mass of said probe as a consequence of said binding, indicates the presence of said second member in said liquid medium,
wherein said immobilized first member is immobilized on a surface of said metal plate by a linking group, having the following general formula (I):

Z—R¹Q (I)

wherein:
Z represents a sulphur-containing moiety which chemically associates with, attaches to, or chemisorbs onto the surface of said metal plate;
R¹ represents a connecting group;
Q is a functional group which forms a covalent bond with a moiety of said first member of said recognition pair.

10. A method for determining binding between a first member of a recognition pair and a second member of a recognition pair, said recognition pair being a pair selected from the group consisting of antigen-antibody, liqand-receptor, sugar-pectin, biotin-avidin, enzyme-substrate, oligonucleotide-oligonucleotide with a complementary sequence, oligonucleotide-protein, and oligonucleotide-cell, said second member being initially contained in a liquid medium, comprising the steps of:

(a) providing a probe comprising a piezoelectric crystal, electrodes on two opposite faces of said crystal, and one or more metal plates carried on the surface of said crystal, said metal plates being the same or different than said electrodes and having immobilized thereon by chemical association, chemical attachment or chemisorption a monolayer comprising said first member of said recognition pair;

(b) measuring an initial resonance frequency of said probe;

(c) contacting said probe with a liquid medium containing said second member for an amount of time sufficient to allow binding between said first member and said second member; and (d) measuring a second resonance frequency, whereby a lower second resonance frequency, as compared to the initial resonance frequency, which results from an increase in mass of said probe as a consequence of said binding, indicates the presence of said second member in said liquid medium, wherein said immobilized first member has or is linked to a group which changes its isomerization state as a result of exposure to energy, said group having a first and a second isomerization state and converts from said first state to said second state upon exposure to a first energy type and from said second state to said first state upon exposure to a second energy type, wherein, in said first state, said immobilized first member has a high affinity of binding to said second member, and in said second state, said immobilized first member has a low affinity of binding to said second member.

11. A method for determining an analyte in a liquid medium, comprising:

(a) providing a probe comprising a piezoelectric crystal, electrodes on two opposite faces of the crystal, and one or more metal plates carried on the surface of said crystal, said metal plates being the same or different than said electrodes and having immobilized thereon by chemical association, chemical attachment or chemisorption a monolayer comprising an immobilized first member bound to a second member of a recognition pair, said second member being capable of binding to an analyte, wherein the binding between said second member and said analyte being competitive to the binding of said second member to said immobilized first member, said recognition pair being selected from a group consisting of antigen-antibody, ligand-receptor, sugar-lectin, biotin-avidin, enzyme-substrate, oligonucleotide-oligonucleotide with a complementary sequence, oligonucleotide-protein, and oligonucleotide-cell;

(b) measuring an initial resonance frequency of said probe;

(c) mixing a liquid medium with a solution containing said second member to form a mixture, whereby the presence of said analyte in said liquid medium causes binding of said analyte to said second member;

(d) contacting the mixture obtained in step (c) with said probe for an amount of time sufficient to allow binding of said second member to said immobilized first member; and (e) measuring a second resonance frequency of said probe, whereby a second resonance frequency lower than the initial frequency indicates binding of said second member to said immobilized first member with a consequent increase of mass of said probe, and deducing therefrom the presence of said analyte in said liquid medium, wherein said analyte is a molecule suspended or dissolved in a gas, the method further comprising the step of passing a gas containing a sample of suspended or dissolved molecules through a liquid to determine the presence of said analyte in said liquid.

12. A method for determining an analyte in a liquid medium, comprising:

(a) providing a probe comprising a piezoelectric crystal, electrodes on two opposite faces of the crystal, and one or more metal plates carried on the surface of said crystal, said metal plates being the same or different than said electrodes and having immobilized thereon by chemical association, chemical attachment or chemisorption a monolayer comprising an immobilized first member bound to a second member of a recognition pair, said second member being capable of binding to an analyte, wherein the binding between said second member and said analyte being competitive to the binding of said second member to said immobilized first member, said recognition pair being selected from a group consisting of antigen-antibody, ligand-receptor, sugar-lection, biotin-avidin, enzyme-substrate, oligonucleotide-oligonucleotide with a complementary sequence, oligonucleotide-protein, and oligonucleotide-cell;

(b) measuring an initial resonance frequency of said probe;

(c) mixing a liquid medium with a solution containing said second member to form a mixture, whereby the presence of said analyte in said liquid medium causes binding of said analyte to said second member;

(d) contacting the mixture obtained in step (c) with said probe for an amount of time sufficient to allow binding of said second member to said immobilized first member; and (e) measuring a second resonance frequency of said probe, whereby a second resonance frequency lower than the initial frequency indicates binding of said second member to said immobilized first member with a consequent increase of mass of said probe, and deducing therefrom the presence of said analyte in said liquid medium, wherein said immobilized first member is immobilized on a surface of said metal plate by a linking group, having the following general formula (I):

$$Z—R^1Q \qquad (I)$$

wherein:

Z represents a sulphur-containing moiety which chemically associates with, attaches to, or chemisorbs onto the surface of said metal plate;

$R^1$ represents a connecting group;

Q is a functional group which forms a covalent bond with a moiety of said first member of said recognition pair.

13. A method for determining an analyte in a liquid medium, comprising:

(a) providing a probe comprising a piezoelectric crystal, electrodes on two opposite faces of the crystal, and one or more metal plates carried on the surface of said crystal, said metal plates being the same or different than said electrodes and having immobilized thereon by chemical association, chemical attachment or chemisorption a monolayer comprising an immobilized first member bound to a second member of a recognition pair, said second member being capable of binding to an analyte, wherein the binding between said second member and said analyte being competitive to the binding of said second member to said immobilized first member, said recognition pair being selected from a group consisting of antigen-antibody, ligand-receptor, sugar-lectin, biotin-avidin, enzyme-substrate, oligonucleotide-oligonucleotide with a complementary sequence, oligonucleotide-protein, and oligonucleotide-cell;

(b) measuring an initial resonance frequency of said probe;

(c) mixing a liquid medium with a solution containing said second member to form a mixture, whereby the presence of said analyte in said liquid medium causes binding of said analyte to said second member;

(d) contacting the mixture obtained in step (c) with said probe for an amount of time sufficient to allow binding of said second member to said immobilized first member; and (e) measuring a second resonance frequency of said probe, whereby a second resonance frequency lower than the initial frequency indicates binding of said second member to said immobilized first member with a consequent increase of mass of said probe, and deducing therefrom the presence of said analyte in said liquid medium, wherein said immobilized first member has or is linked to a group which changes its isomerization state as a result of exposure to energy, said group having a first and a second isomerization state and converts from said first state to said second state upon exposure to a first energy type and from said second state to said first state upon exposure to a second energy type, wherein, in said first state, said immobilized first member has a high affinity of binding to said second member, and in said second state, said immobilized first member has a low affinity of binding to said second member.

14. A probe, comprising a piezoelectric crystal, electrodes on two opposite faces of the crystal, and one or more metal plates carried on the surface of said crystal, said metal plates being the same or different than said electrodes and having immobilized thereon by chemical association, chemical attachment or chemisorption a first member of a recognition pair, said recognition pair being selected from the group consisting of antigen-antibody, ligand-receptor, sugar-lectin, biotin-avidin, enzyme-substrate, oligonucleotide-oligonucleotide with a complementary sequence, oligonucleotide-protein, and oligonucleotide-cell.

* * * * *